United States Patent
Min et al.

(10) Patent No.: US 8,682,450 B2
(45) Date of Patent: Mar. 25, 2014

(54) SYSTEMS AND METHODS FOR CONTROLLING NEUROSTIMULATION OF ACUPUNCTURE SITES USING AN IMPLANTABLE CARDIAC RHYTHM MANAGEMENT DEVICE

(75) Inventors: Xiaoyi Min, Thousand Oaks, CA (US); Stuart Rosenberg, Castaic, CA (US); Taraneh Ghaffari Farazi, San Jose, CA (US); Timothy A. Fayram, Gilroy, CA (US)

(73) Assignee: Pacesetter, Inc., Sylmar, CA (US)

(*) Notice: Subject to any disclaimer, the term of this patent is extended or adjusted under 35 U.S.C. 154(b) by 0 days.

(21) Appl. No.: 13/563,417

(22) Filed: Jul. 31, 2012

(65) Prior Publication Data

US 2014/0039238 A1 Feb. 6, 2014

(51) Int. Cl.
*A61N 1/05* (2006.01)

(52) U.S. Cl.
USPC .............................. 607/116; 600/548

(58) Field of Classification Search
USPC .......................... 600/548; 607/116
See application file for complete search history.

(56) References Cited

U.S. PATENT DOCUMENTS

| | | | |
|---|---|---|---|
| 5,199,428 A | 4/1993 | Obel et al. | |
| 5,211,175 A | 5/1993 | Gleason et al. | |
| 5,425,752 A | 6/1995 | Vu'Nguyen | |
| 5,623,936 A | 4/1997 | McClure | |
| 5,792,187 A | 8/1998 | Adams | |
| 5,908,392 A | 6/1999 | Wilson et al. | |
| 6,134,470 A | 10/2000 | Hartlaub | |
| 6,349,233 B1 | 2/2002 | Adams | |
| 6,473,647 B1 | 10/2002 | Bradley | |
| 6,480,733 B1 | 11/2002 | Turcott | |
| 7,079,891 B1 | 7/2006 | Kroll | |
| 7,103,412 B1 | 9/2006 | Kroll | |
| 7,113,822 B1 | 9/2006 | Kroll | |
| 7,164,944 B1 | 1/2007 | Kroll et al. | |
| 7,248,925 B2 | 7/2007 | Bruhns et al. | |
| 7,272,436 B2 | 9/2007 | Gill et al. | |
| 7,295,873 B1 | 11/2007 | Min et al. | |
| 7,297,114 B2 | 11/2007 | Gill et al. | |
| 7,321,792 B1 * | 1/2008 | Min et al. ........................ 607/3 |
| 7,357,775 B1 | 4/2008 | Koh | |
| 7,373,204 B2 | 5/2008 | Gelfand et al. | |
| 7,400,920 B1 | 7/2008 | Gill et al. | |
| 7,430,447 B2 | 9/2008 | Min et al. | |
| 7,440,804 B1 | 10/2008 | Min et al. | |

(Continued)

FOREIGN PATENT DOCUMENTS

WO 0141869 A1 6/2001

OTHER PUBLICATIONS

Cardinal, Rene et al., "Spinal cord stimulation suppresses bradycardias and atrial tachyarrhythmias induced by mediastinal nerve stimulation in dogs," Am J Physiol Regul Integr Comp Physiol. 2006;291:R1369-R1375.

(Continued)

*Primary Examiner* — Christopher D Koharski
*Assistant Examiner* — Michael Carey

(57) ABSTRACT

Techniques are provided for use with an implantable cardiac rhythm management (CRMD) system equipped to deliver neurostimulation to acupuncture sites within anterior regions of the neck, thorax or abdomen of the patient. Parameters associated with the health of the patient are detected, such as parameters indicative of arrhythmia, heart failure and hypertension.

26 Claims, 21 Drawing Sheets

(56) References Cited

U.S. PATENT DOCUMENTS

| | | |
|---|---|---|
| 7,462,150 B1 | 12/2008 | Bharmi et al. |
| 7,502,644 B2 | 3/2009 | Gill et al. |
| 7,529,580 B2 | 5/2009 | Gill et al. |
| 7,606,618 B1 | 10/2009 | Bornzin et al. |
| 7,621,036 B2 | 11/2009 | Cros et al. |
| 7,756,572 B1 | 7/2010 | Fard et al. |
| 7,794,404 B1 | 9/2010 | Gutfinger et al. |
| 7,826,899 B1 | 11/2010 | Ryu et al. |
| 7,869,870 B1 | 1/2011 | Farazi |
| 7,953,479 B2 | 5/2011 | Wenzel et al. |
| 8,021,307 B2 | 9/2011 | White et al. |
| 8,032,212 B2 | 10/2011 | Bornzin et al. |
| 8,050,760 B2 | 11/2011 | Cholette |
| 8,090,435 B2 | 1/2012 | Gill et al. |
| 8,090,444 B2 | 1/2012 | Min et al. |
| 8,092,386 B1 | 1/2012 | Wenzel et al. |
| 8,147,416 B2 | 4/2012 | Fayram et al. |
| 8,162,842 B2 | 4/2012 | Gill et al. |
| 8,208,999 B2 | 6/2012 | Wenzel et al. |
| 2003/0078642 A1 | 4/2003 | Malaney et al. |
| 2003/0216792 A1 | 11/2003 | Levin et al. |
| 2006/0287602 A1 | 12/2006 | O'Brien et al. |
| 2007/0156056 A1 | 7/2007 | Min et al. |
| 2007/0265680 A1 | 11/2007 | Liu |
| 2008/0091114 A1 | 4/2008 | Min et al. |
| 2008/0288013 A1 | 11/2008 | Schecter |
| 2009/0062667 A1 | 3/2009 | Fayram et al. |
| 2009/0099467 A1 | 4/2009 | Toren-Herrinton et al. |
| 2009/0143811 A1 | 6/2009 | Chi |
| 2009/0264783 A1 | 10/2009 | Xi et al. |
| 2009/0299211 A1 | 12/2009 | Wenzel et al. |
| 2010/0049274 A1 | 2/2010 | Cholette |
| 2010/0057158 A1 | 3/2010 | Rodriguez et al. |
| 2010/0081952 A1 | 4/2010 | Gill et al. |
| 2010/0121401 A1 | 5/2010 | Min et al. |
| 2010/0137939 A1 | 6/2010 | Liu |
| 2011/0137369 A1 | 6/2011 | Ryu et al. |
| 2011/0184304 A1 | 7/2011 | Koh |
| 2011/0208077 A1 | 8/2011 | Soriano et al. |
| 2012/0136406 A1 | 5/2012 | Min |

OTHER PUBLICATIONS

Cho Z. H. et al., "New findings of the correlation between acupoints and corresponding brain cortices using functional MRI," Proc. Natl. Acad. Sci. USA. 1998;95(5):2670-2673.

Fujiwara, Hideomi MD et al., "The Influence of Low Frequency Acupuncture on a Demand Pacemaker," Chest. 1980;78(1):96-97.

Hsieh Jen-Chen et al., "Activation of the hypothalamus characterizes the acupuncture stimulation at the analgesic point in human: a positron emission tomography study," Neurosci. Lett.. 2001;307(2):105-108.

Issa, Ziad F. et al., "Thoracic Spinal Cord Stimulation Reduces the Risk of Ischemic Ventricular Arrhythmias in a Postinfarction Heart Failure Canine Model," Circulation. 2005;111(24):3217-3220.

Jacques, Frederic MD et al., "Spinal Cord Stimulation Causes Potentiation of Right Vagus Nerve Effects on Atrial Chronotropic Function and Repolarization in Canines," J Cardiovasc Electrophysiol. 2011;22:440-447.

Lopshire, John C. et al., "Spinal Cord Stimulation Improves Ventricular Function and Reduces Ventricular Arrhythmias in a Canine Postinfarction Heart Failure Model," Circulation. 2009;120:286-294.

Olgin, Jeffrey E. MD et al., "Effects of Thoracic Spinal Cord Stimulation on Cardiac Autonomic Regulation of the Sinus and Atrioventricular Nodes," J Cardiovasc Electrophysiol. 2002;13(5):475-481.

Siedentopf, Christian M. et al., "Functional magnetic resonance imaging detects activation of the visual association cortex during laser acupuncture of the foot in humans," Neurosci. Lett.. 2002;327(1):53-56.

Wu, Ming-Ting MD et al., "Central Nervous System Pathway for Acupuncture Stimulation: Localization of Processing with Functional MR Imaging of the Brain—Preliminary Experience," Radiology. 1999;212:133-141.

* cited by examiner

PERIODIC SELECTION/ADJUSTMENT OF NEUROSTIMULATION LEADS AND PARAMETERS APPLICABLE TO VARIOUS NEUROSTIMULATION PROCEDURES

IN RESPONSE TO THE NEED FOR NEUROSTIMULATION, SELECT STIMULATION ELECTRODES BASED ON THE LOCATION OF THE ACUPUNCTURE SITE WHERE STIMULATION IS NEEDED FROM AMONG LEAD ARRANGEMENTS THAT INCLUDE:

– PERCUTANEOUS LEADS HAVING THREE PAIRS OF BIPOLAR ELECTRODES, WITH EACH PAIR AT A DIFFERENT SITE

– TWO STERNUM (STN) LEADS WITH ONE IMPLANTED SUBCUTANEOUSLY AND THE OTHER IMPLANTED UNDER THE STERNUM AND STIMULATED USING ALL CATHODES ON ONE LEAD AND ALL ANODES ON THE OTHER

– STERNUM (STN) LEADS IMPLANTED IN PECTORAL REGIONS OF THE PATIENT (EITHER LEFT OR RIGHT PECTORAL REGIONS)

– STERNUM (STN) LEADS IMPLANTED IN ABDOMINAL REGIONS OF THE PATIENT (EITHER LEFT OR RIGHT ABDOMINAL REGIONS)

1000

DELIVER AND CONTROL STIMULATION TO H1, H2+, H2−, L1, L2, P1 AND P2 SITES (AND SELECTED ADDITIONAL SITES SUCH AS T1−T5, T11−L2) USING THE SELECTED LEAD ARRANGEMENT USING: A SIMULTANEOUS PATTERN; A SEQUENTIAL PATTERN; OR A COMBINATION OF SIMULTANEOUS AND SEQUENTIAL PATTERNS WITH A FREQUENCY IN THE RANGE OF 20−50 HZ; A PULSE WIDTH OF ABOUT 0.2 MS AND A MAXIMUM VOLTAGE OF ABOUT 13.5 V WHILE ADAPTIVELY ADJUSTING THE STIMULATION CONTROL PARAMETERS BY AN AMOUNT SUFFICIENT TO IMPROVE AT LEAST ONE PARAMETER REPRESENTATIVE OF THE HEALTH OF THE PATIENT

SYSTEMS AND METHODS FOR CONTROLLING NEUROSTIMULATION OF ACUPUNCTURE SITES USING AN IMPLANTABLE CARDIAC RHYTHM MANAGEMENT DEVICE

FIELD OF THE INVENTION

The invention generally relates to implantable cardiac rhythm management devices (CRMDs) and, in particular, to techniques for controlling neurostimulation at acupuncture sites using such devices.

BACKGROUND OF THE INVENTION

Various therapies, known to or stemming from traditional Oriental medicine, rely on pressure, needle, electric and/or magnetic stimulation of specific points in the human body. Many of these therapies emphasize energy balancing; consider Chinese acupuncture (Zhen Jiu) which aims to balance a vital energy known as Qi. According to traditional acupuncture, Qi interacts with vital substances such as Xue (blood), Jing (essence), Shen (spirit), and Jin Ye (bodily fluids). For example, Xue follows Qi through the body primarily via twelve main energy ducts called meridians wherein each of these meridians connects to one of twelve organs. Acupuncture models typically show meridians as lines running and occasionally crossing throughout the body wherein individual acupuncture points, or acupoints, fall along the meridians. According to the practice of acupuncture, acupoint stimulation can release blockages, balance Qi and restore the body to its natural state. A practitioner of acupuncture typically stimulates an acupoint through manual manipulation of a fine needle inserted subcutaneously at an acupoint; whereas, a practitioner of acupressure (Zhi Ya) may apply pressure to stimulate an acupoint. More recently, however, electric and/or magnetic energy have been used to stimulate acupoints, for example, consider electroacupuncture, which has generally proven to be more convenient and effective than manual stimulation.

While Western medicine has typically viewed acupuncture relatively simply (e.g., as synonymous with nerve stimulation), recent studies support the Oriental view that meridians and acupoints have special significance. In particular, various studies suggest that acupoint stimulation produces a result essentially different than that of non-acupoint stimulation. To elucidate such differences, researchers have begun using functional magnetic resonance imaging (fMRI) or positron emission tomography (PET) to map brain activity responsive to stimulation at acupoints and non-acupoints. A study by Cho et al., "New findings of the correlation between acupoints and corresponding brain cortices using functional MRI," Proc. Natl. Acad. Sci. USA, 95(5):2670-2673 (1998), showed that ancient acupuncture literature correctly associated acupoints with particular organs or brain activity. More specifically, Cho et al. demonstrated that stimulation at acupoint BL.67 (Zhi Yin), located on the foot and known for treatment of eye disorders, activated the occipital lobes whereas stimulation of non-acupoints (e.g., points displaced by two cm to five cm) did not activate the occipital lobes. A later study by Siedentopf et al., "Functional magnetic resonance imaging detects activation of the visual association cortex during laser acupuncture of the foot in humans," Neurosci. Lett., 327(1):53-56 (2002), confirmed that acupoint stimulation at BL.67 activated the visual cortex. These studies lend credence to a wealth of traditional therapies based on acupoint stimulation.

Another study, by Wu et al., "Central nervous system pathway for acupuncture stimulation: localization of processing with functional MR imaging of the brain—preliminary experience," Radiology, 212:133-141 (1999), examined acupuncture at two acupoints, well-known for analgesia, and "minimal" acupuncture at non-acupoints (e.g., points displaced by 2 cm to 3 cm). Wu et al. reported that acupuncture at LI.4 (Hegu) and ST.36 (Zusanli) produced bradycardia and activation of the hypothalamus and nucleus accumbens and deactivation of the rostral part of the anterior cingulated cortex, amygdala formation, and hippocampal complex; whereas, minimal acupuncture at the non-acupoints produced activation of the supplementary motor cortex, parietal operculum, and frontal operculum. Wu et al. also detected a more extensive activation of the hypothalamus for stimulation of the LI.4 acupoint compared to the ST.36 acupoint and noted that this result coincides with clinical observations that show stimulation at LI.4 produces a stronger analgesic effect than stimulation at ST.36. On the basis of their results, Wu et al. hypothesized that bradycardia is characteristic of an acupuncture-related autonomic response and that acupuncture analgesia is associated with deactivation of limbic areas and attenuation of the affective response to pain. Wu et al. also recognized that acupuncture often has analgesic and non-analgesic effects. A later study by Hsieh et al., "Activation of the hypothalamus characterizes the acupuncture stimulation at the analgesic point in human: a positron emission tomography study," Neurosci. Lett., 307(2):105-108 (2001), also examined stimulation at the LI.4 acupoint and a non-acupoint. Hsieh et al. found that stimulation of the LI.4 acupoint activated the hypothalamus while stimulation of the non-acupoint did not. These studies support the traditional practice of acupoint stimulation for treatment of pain as well as other disorders.

Overall, studies using modern imaging modalities have effectively demonstrated that acupoint stimulation can produce therapeutic action. In the realm of cardiac pacing and/or stimulation therapies, acupoint stimulation holds promise. However, Fujiwara et al., as reported in "The influence of low frequency acupuncture on a demand pacemaker," Chest, 78:96-97 (1980), found that low frequency acupuncture caused electromagnetic interference capable of interfering with demand sensing. Indeed, electroacupuncture is often contraindicated for patients having implanted pacing and/or stimulation devices, especially devices that rely on sensing. Therefore, a need exists for methods, devices and/or systems that allow cardiac pacing and/or stimulation therapy patients to benefit from electric and/or magnetic acupoint stimulation therapy.

U.S. Pat. No. 7,321,792 to Min et al., entitled "Pacing Therapy and Acupuncture," addressed some of these needs. In various examples described therein, an implantable cardiac therapy device detects the need for anti-arrhythmia therapy and communicates with an implanted slave device, which, in turn, delivers power to an acupuncture point that may have an analgesic, anti-arrhythmic or other beneficial effect. Alternatively, the slave device notifies the patient (or caregiver) to administer a potentially beneficial acupuncture therapy. In one example, an implantable cardioverter defibrillator (ICD) detects an arrhythmia that warrants a defibrillation shock (such as an episode of atrial fibrillation (AF) that warrants a cardioversion shock) and then communicates pertinent information to an external device to warn the patient of caregiver. Stimulation is delivered via an external device at an acupuncture site in the arm in an effort to minimize pain associated with the imminent shock.

Hence, the Min et al. patent sets forth various techniques for providing stimulation at acupuncture points. Some aspects of the present invention are directed to expanding or modifying these stimulation techniques to achieve additional or alternative benefits, particularly for use with a CRMD.

Another stimulation technique that may be used in conjunction with a CRMD is spinal cord simulation (SCS.) Several studies have connected SCS with cardiac electrophysiology. For example, studies by Olgin et al. and Jacques at al. indicated that SCS blunts the effects of sympathetic stimulation and enhances the effects of vagal stimulation. (See, Olgin et al., JCE 2002 and Jacques et al. JCE 2011.) Cardinal et al. indicated that SCS suppressed neurally-mediated atrial brady- and tachyarrhythmias. (See, Cardinal et al., AJP Reg Integ Comp Physiol 2006.) Issa et al. and Lopshire et al. showed results indicating SCS prevented ischemia related ventricular tachyarrhythmias. (See, Issa at al., Circ 2005 and Lopshire et al., Circ 2009.) Insofar as heart failure is concerned, Lopshire at al. (Circ 2009) studied SCS in systolic heart failure with myocardial infarction and rapid RV pacing. Their results showed therapeutic benefits of SCS on clinical parameters of decreased heart rate, increase in systolic blood pressure, decrease in weight gain, and increase in oxygen saturation. The results also showed a decrease in spontaneous and ischemic-challenged ventricular tachycardia (VT), brain natriuretic peptide and norepinephrine, and reverse remodeling with increase in left ventricular (LV) ejection fraction and decrease in LV dimension. Effect of SCS alone was shown to be greater than SCS with medications.

At least some implantable systems have been proposed that employ both a CRMD and a SCS device. See, for example, U.S. Pat. Nos. 6,349,233 and 5,792,187, both to Adams. SCS for use in conjunction with an implanted pacemaker or heart monitor to treat angina (activated in response to detection of ischemia) is discussed in U.S. Pat. No. 5,199,428 issued to Obel et al. See, also, U.S. Pat. No. 6,134,470 to Hartlaub.

Accordingly, both SCS and acupuncture represent promising techniques that may be exploited in connection with cardiac rhythm management and heart failure management. Preferably, the CRMD would control the operation of the SCS or acupuncture device to coordinate cardiac rhythm management and heart failure management. However, it may be impractical (at least in some cases) to implant both a SCS device and a CRMD within a given patient, especially if the CRMD is intended to control the operation of the SCS. In this regard, the CRMD is typically implanted within an anterior pectoral region of the chest near the heart whereas a SCS device is usually implanted in the buttocks or abdomen with its leads along the spinal cord. Likewise, it may be impractical to implant both a CRMD and a separate acupuncture stimulation controller within a patient, at least for stimulating acupuncture points remote from the implant location of the CRMD.

Accordingly, aspects of the invention are directed to providing a more practical implantable system that uses a CRMD to control neurostimulation without the need for a separate SCS controller or a separate acupoint neurostimulation controller. Other aspects of the invention are directed to greatly expanding the capability of a CRMD to coordinate neurostimulation at acupuncture sites to achieve a range of benefits such as: modulating cardiac functions to prevent or mitigate heart failure progression; preventing or mitigating arrhythmia; improving the success rate of antitachycardia pacing (ATP); controlling hypertension; controlling respiration to treat Cheyne-Stokes respiration (CSR) and sleep apnea; and reducing pain from angina or from AF shocks or VT/ventricular fibrillation (VF) shocks.

SUMMARY

In an exemplary embodiment, a method is provided for use with an implantable medical system for implant within a patient wherein the system is equipped to deliver neurostimulation to acupuncture sites within anterior regions of the neck, thorax or abdomen of the patient. Briefly, at least one parameter associated with the health of the patient is detected by the system, such as a parameter representative of arrhythmia, heart failure or hypertension. Neurostimulation is then delivered to one or more acupuncture sites within anterior regions of the neck, thorax or abdomen in response to the parameter associated with the health of the patient. The implantable system may include a pacemaker, implantable cardioverter/defibrillator (ICD), cardiac resynchronization therapy (CRT) device or other CRMD. The neurostimulation is delivered, depending upon the detected parameter and the needs of the patient, to the following acupuncture sites: H1, H2+ and H2− (i.e. along sternum between rib two and rib three and at two sites below the rib cage); L1 and L2 (i.e. along the sternum between rib one and rib two and a site at the clavicle); and P1 and P2 (at opposing sides of the thyroid cartilage.) By providing for delivery of neurostimulation to the aforementioned acupuncture sites (which are located within anterior anatomical regions of the patient), the CRMD can be equipped to control the stimulation using neurostimulation leads directly connected to the housing of the CRMD (which is typically implanted in the left anterior quadrant of the thorax below the collar bone.) By controlling the stimulation based on parameters associated with the health of the patient, the location and pulse characteristics of the neurostimulation can be selected and adjusted to achieve various goals directed to improving patient health such as mitigating heart failure, suppressing arrhythmia, controlling hypertension, addressing cardiac ischemia, controlling respiration to treat CSR or sleep apnea, and reducing pain from angina or from AF shocks or VT/VF shocks.

In an illustrative embodiment, the CRMD is equipped with a set of percutaneous or subcutaneous neurostimulation leads positioned to deliver electrical, magnetic or thermal stimulation at or near the H1, H2+, H2−, L1, L2, P1 and P2 acupuncture sites so that particular sites can be selected based on the health of the patient as indicated by the detected parameters. For heart failure, the device uses various pacing/sensing leads to detect impedance (Z) parameters, evoked response (ER) parameters, intracardiac electrogram (IEGM) conduction delay parameters or cardiogenic impedance (Zc) conduction delay parameters, from which an indication of heart failure is derived. If suitable pressure sensors or proxies are available, then left atrial (LA) pressure, pulmonary artery (PA) pressure or right ventricular (RV) pressure may additionally or alternatively be exploited to assess heart failure. If heart failure is indicated, neurostimulation is selectively delivered at one or more of H1, H2+ and H2− sites in an effort to mitigate heart failure, prevent its progression and, preferably, achieve a reverse modeling of the heart tissues. To this end, the CRMD controls the location of neurostimulation (i.e. the particular site: H1, H2+, H2− or some combination thereof) and the neurostimulation control parameters (e.g. pulse frequency, pulse width, pulse amplitude, pulse pattern and pulse configuration.) The pulse pattern may specify, e.g., a simultaneous pattern, a sequential pattern or a combination thereof. The pulse configuration may specify the particular electrodes of the neurostimulation leads to be used as anodes or cathodes. Any or all of the neurostimulation parameters may be adjusted in a feedback loop over time while heart failure parameters are periodically detected and assessed so as to identify preferred or optimal neurostimulation parameters to address heart failure.

For arrhythmia, the device may use pacing/sensing leads to detect IEGM signals indicative of AF, VF, atrial tachycardia (AT) or other arrhythmias, as well as related parameters such as a premature atrial contraction (PAC) counts, a premature ventricular contraction (PVC) counts, heart rate variability (HRV) values or heart rate turbulence (HRT) values, from which an indication of an arrhythmia and its severity is derived. If an arrhythmia is detected, neurostimulation is selectively delivered at one or more of the H1, H2+ and H2− sites in an effort to suppress the arrhythmia. If the arrhythmia is AF or AT, the device can determine an AT/AF burden and control the neurostimulation in an effort to reduce the burden. If ATP is delivered by the device, the neurostimulation can be controlled in an effort to improve an ATP success rate. The various neurostimulation control parameters may be adjusted in a feedback loop while arrhythmia is detected and assessed to identify preferred or optimal neurostimulation parameters to address the arrhythmia. Moreover, if shocks are needed for AF or VF, neurostimulation may be delivered at the H1, H2+ and H2− sites in an attempt to mitigate the pain of the shocks.

For hypertension, the device may use the pacing/sensing leads or implanted sensors to detect pulmonary artery pressure (PAP), left atrial pressure (LAP) or other parameters indicative of hypertension. If no sensors are available, the device may estimate PAP and LAP based on suitable proxies. For example, PAP pressure may be derived from a maximum rate of change in right ventricular (RV) pressure (RV dP/dt max.) If hypertension is indicated, neurostimulation is selectively delivered at one or more of the P1 and P2 sites in an effort to reduce the hypertension. As with heart failure and arrhythmia, any or all of the neurostimulation control parameters can be adjusted in a feedback loop to improve stimulation efficacy.

For CSR or sleep apnea, the device may use the pacing/sensing leads to detect thoracic impedance signals indicative of CSR or apnea. If CSR or apnea is indicated, neurostimulation is selectively delivered at one or more of the L1 and L2 sites in an effort to suppress of mitigate the condition, and the neurostimulation parameters are adjusted in a feedback loop as needed. For cardiac ischemia, the device may use the pacing/sensing leads to detect IEGM signals indicative of ischemia (including infarction) or other coronary blood circulation problems. For angina, the device may receive input from the patient or caregiver indicating the onset of pain due to angina. If ischemia or angina is indicated, neurostimulation is selectively delivered at one or more of the H1, H2+ and H2− sites and the stimulation is adjusted in a feedback loop to mitigate the condition or any pain associated with it.

Insofar as the neurostimulation leads and configurations are concerned, in one example neurostimulation is delivered using percutaneous leads having three pairs of bipolar electrodes, with each pair at a different site. In another example, neurostimulation is delivered using two sternum (STN) leads with one implanted subcutaneously and the other implanted under the sternum and stimulated using all cathodes on one lead and all anodes on the other. In some implementations, the sternum leads are implanted in pectoral regions of the patient (either left or right pectoral regions) or in the abdominal regions of the patient (either left or right abdominal regions.) In some examples, pulse frequencies are in the range of 20-50 Hz, the pulse width is about 0.2 ms and the maximum voltage of the pulses is about 13.5 volts (V). In examples where magnetic neurostimulation is exploited, the stimulation leads may include surgical patches made with materials similar to those used for spinal cord stimulation (SCS). For example, STN patches may be provided on two STN leads (subcutaneous and sub-sternum) in parallel. Paired current loops from the leads are generated to induce magnetic field B lines through the stimulating sites. Still further, subcutaneous "finger arrays" may be exploited for stimulating acupuncture sites in the abdomen.

System and method examples are described in detail below.

BRIEF DESCRIPTION OF THE DRAWINGS

The above and further features, advantages and benefits of the invention will be apparent upon consideration of the descriptions herein taken in conjunction with the accompanying drawings, in which:

FIG. 12 is an exemplary embodiment of the general neurostimulation technique of FIG. 2, which particularly illustrates methods for selecting neurostimulation lead configurations and neurostimulation control parameters;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of CRMD with Acupuncture Site Neurostimulation Controller

Figure 1:
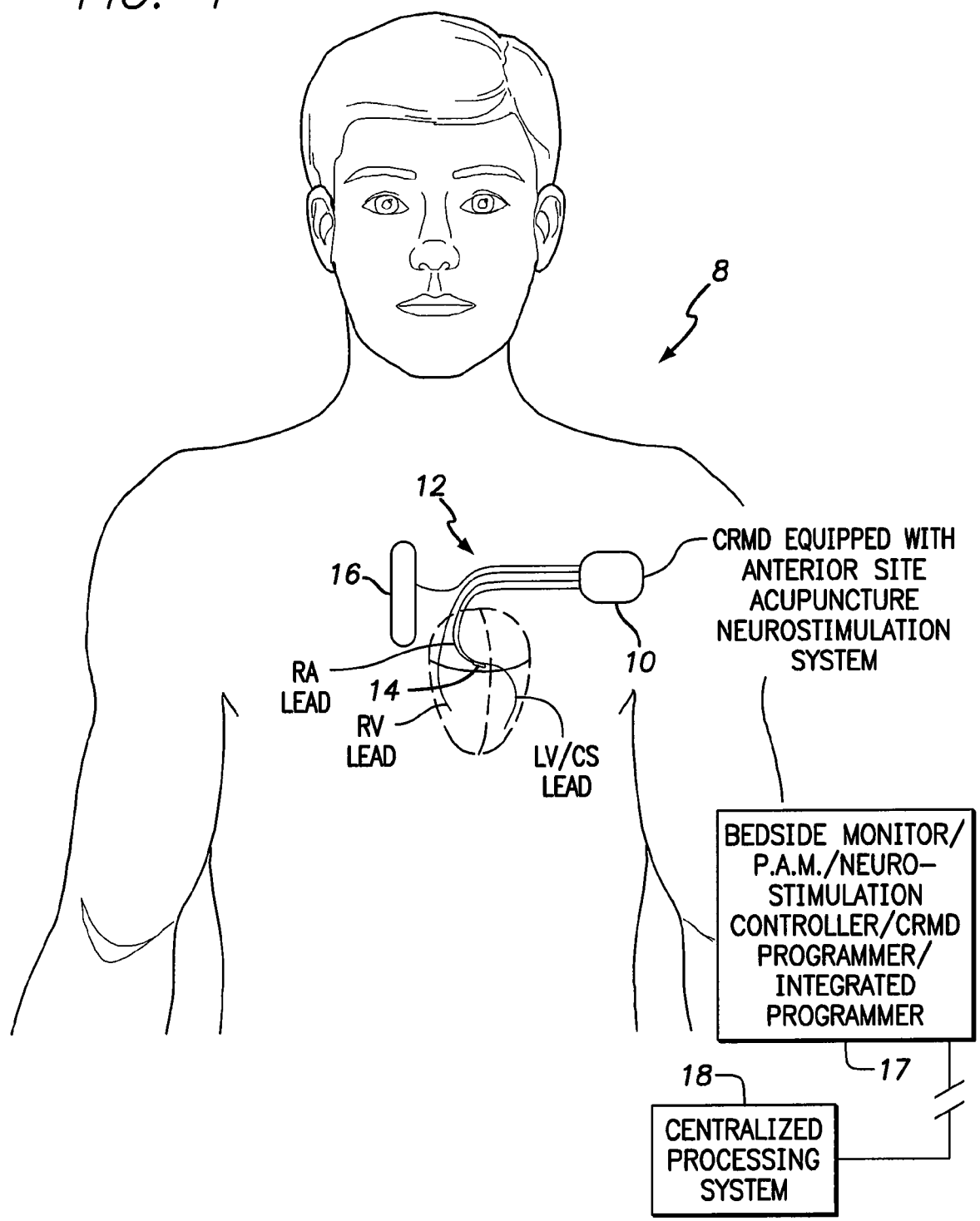
FIG. 1 illustrates pertinent components of a CRMD equipped with an anterior acupuncture site neurostimulation system for stimulation of acupuncture points within anterior regions of the neck, thorax and abdomen.

FIG. 1 illustrates an implantable medical system 8 having a CRMD 10 equipped for delivering and controlling neurostimulation to acupuncture sites, particularly sites within generally anterior regions of the neck, thorax and abdomen. The neurostimulation is controlled based on parameters representative of patient health detected by the CRMD, such as parameters derived from IEGM signals sensed via a set of cardiac leads 12 or from physiological parameters detected via one or more physiological sensors 14. In this example, sensor 14 is shown mounted to one of the cardiac leads but it may be implanted elsewhere depending upon the parameters to be detected. Based on the detected parameters, CRMD 10 controls neurostimulation delivered to selected acupuncture sites via a neurostimulation device 16. In this example, device 16 is implanted within the anterior thoracic cavity near the sternum for stimulating the H1, H2+, H2−, L1 and/or L2 sites. In other examples, the neurostimulation devices may additionally or alternatively be mounted elsewhere, such as in the anterior region of the neck for stimulating the P1 and P2 sites. (See, FIGS. 13-16, discussed below, for a more precise illustration of exemplary neurostimulation leads and sites.) Depending upon the implementation, the neurostimulation leads may be equipped for electrical, magnetic or thermal stimulation, or some combination thereof.

Figure 20:
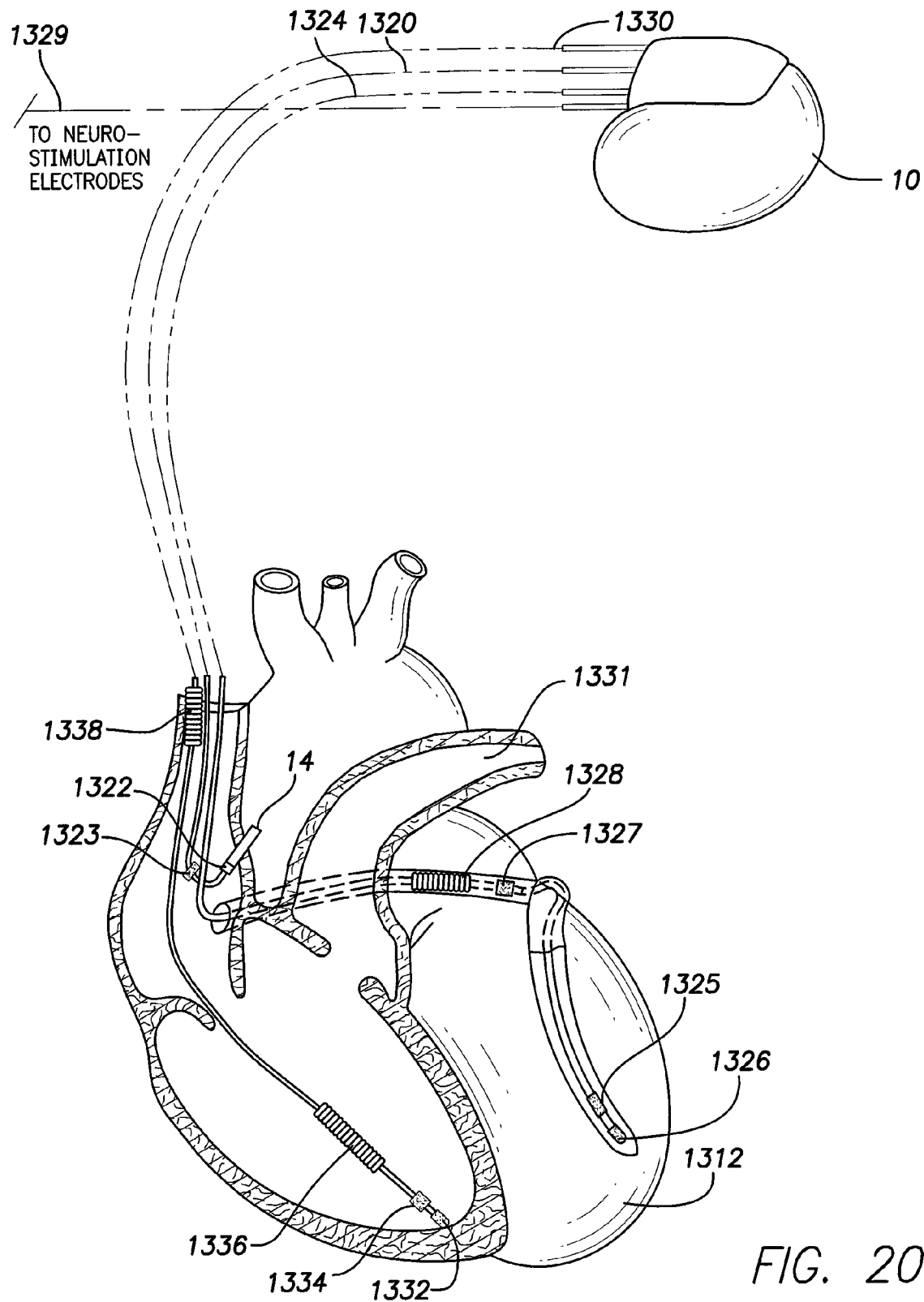
FIG. 20 is a simplified, partly cutaway view of the heart of a patient, illustrating the exemplary CRMD of FIG. 1, along with leads implanted in the heart of the patient and another lead for neurostimulation.

In so far as cardiac pacing/sensing is concerned, FIG. 1 illustrates three exemplary leads (LV, RV and RA) for sensing IEGM signals or measuring impedance (Z). A more complete set of leads is illustrated in FIG. 20, described below. In the example of FIG. 1, physiological sensor 14 is shown mounted to the end of the RA lead for transseptal implant into the left atrium (LA) but additional or alternative sensor locations may be exploited. It should be understood that the actual location of the sensor(s) will depend upon the particular physiological parameter or parameters to be detected. As such, the location of the sensor of FIG. 1 is merely exemplary. Note also that, in some cases, the sensor will be a component of the CRMD itself. This is particularly common for sensors configured to sense physiological parameters based on an analysis of electrical signals detected using the leads 12. For example, certain hemodynamic sensors are designed to analyze impedance signals detected using the leads. This will be discussed in detail below.

Diagnostic data pertaining to neurostimulation or other therapies may be transmitted to an external system 17 such as a bedside monitor, personal advisory module (PAM), CRMD programmer, patient neurostimulation controller or an integrated CRMD/neurostimulation controller with integrated features and radiofrequency (RF) telemetry or other suitable external systems. The patient neurostimulation controller may be configured, for example, similar to devices currently in use for allowing a patient to control SCS but modified to allow for patient control of at least some aspects of the neurostimulation provided by the CRMD. For example, if the patient feels pain from angina, the patient may enter commands into the external controller, which then relays the commands to the CRMD for delivering neurostimulation to selected acupuncture sites in an attempt to reduce pain from the angina. External device 17 can also forward diagnostic data or other suitable information via a centralized processing system 18 to the patient's primary care physician. The centralized system may include such systems as the HouseCall™ remote monitoring system or the Merlin@home/Merlin.Net systems of St. Jude Medical. The diagnostic data may pertain to neurostimulation and/or to the various parameters associated with the health of the patient that are detected and analyzed by the CRMD, including parameters pertinent to heart failure, arrhythmia, hypertension, etc. Depending on the parameters, the external device may generate warnings to alert the patient or caregiver, particularly as to any serious condition such as progression of heart failure or detection of significant episodes of arrhythmia or ischemia.

The CRMD may also include an internal warning device for alerting the patient such as a vibrating device or a "tickle" voltage device that, in either case, provides perceptible stimulation to the patient to alert the patient. If a PAM is employed, the PAM can provide audible or visual alarm signals to alert the patient or caregiver, as well as any appropriate textual or graphic displays. In addition, diagnostic information may be stored within the CRMD for subsequent transmission to an external device programmer for review by a clinician during a follow-up session between patient and clinician. The clinician then prescribes appropriate therapies including possible medications. The clinician may also adjust the operation of the CRMD to activate, deactivate or otherwise control any therapies automatically provided by the device.

Additionally, the CRMD may perform a wide variety of pacing and/or defibrillation functions, such as delivering routine pacing for bradycardia or generating and delivering shocks in response to VF (if equipped with defibrillation capability.) Also, in some examples, the device is equipped to deliver CRT. Briefly, CRT seeks to normalize asynchronous cardiac electrical activation and resultant asynchronous contractions associated with congestive heart failure (CHF) by delivering synchronized pacing stimulus to both ventricles. The stimulus is synchronized so as to improve overall cardiac function. This may have the additional beneficial effect of reducing the susceptibility to life-threatening tachyarrhythmias.

Overview of Acupuncture Site Neurostimulation Control Techniques

Figure 2:
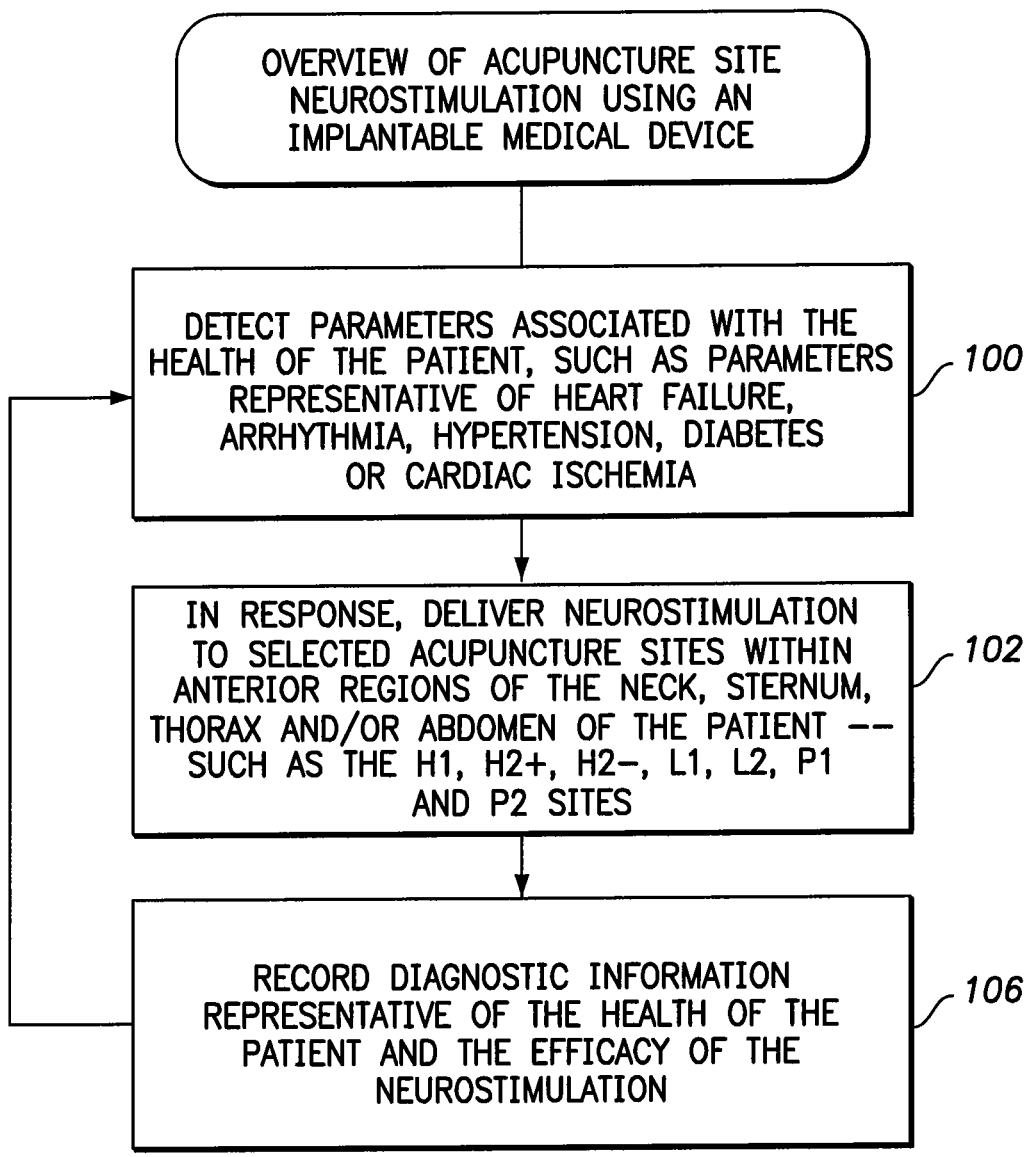
FIG. 2 provides an overview of the method for delivering and controlling neurostimulation performed by the system of FIG. 1.

FIG. 2 broadly summarizes neurostimulation control procedures that may be implemented by the CRMD of FIG. 1 or other suitable equipped implantable medical systems. Initially, at step 100, the CRMD detects parameters associated with the health of the patient, such as parameters representative of heart failure, arrhythmia, hypertension or cardiac ischemia. Techniques for detecting these or other conditions will be set forth in the examples described below. At step 102, in response thereto, the CRMD delivers neurostimulation to selected acupuncture sites within anterior regions of the neck, thorax (including sites along the sternum) and/or abdomen of the patient—such as the H1, H2+, H2−, L1, L2, P1 and P2 sites. For example, the particular site for neurostimulation (e.g. H1, L1, etc.) may be selected by the CRMD based on the detected parameter (and any health problems associated therewith) and then the stimulation is controlled in an effort to address the health problem. As just one example, in response to parameters indicative of heart failure, neurostimulation may be delivered to the H1, H2+, H2− sites in an effort to mitigate heart failure.

Figure 3:
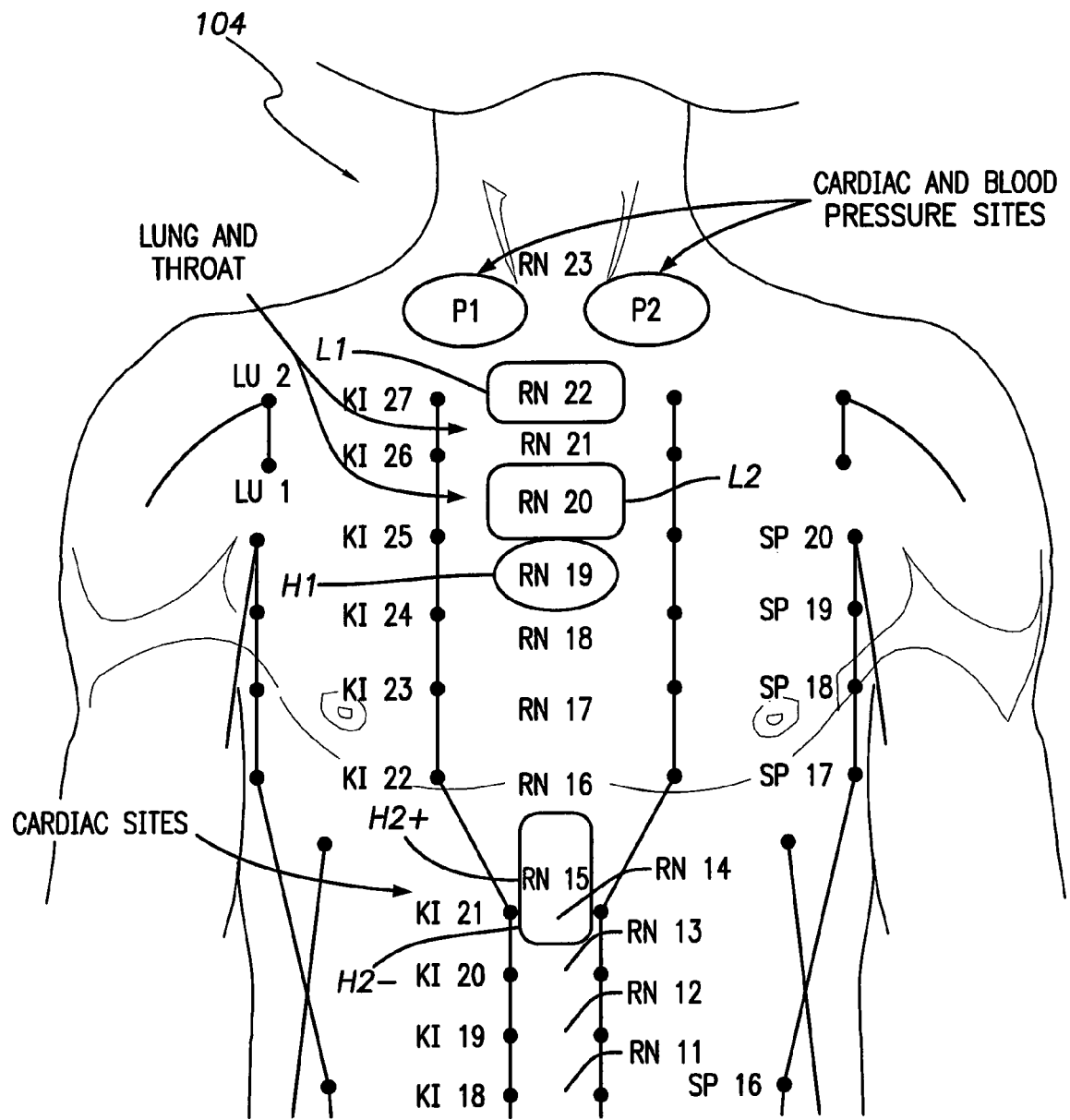
FIG. 3 illustrates exemplary acupuncture sites within anterior regions of the neck and thorax that may be selected for use with the technique of FIG. 2, particularly the H1, H2+, H2−, L1, L2, P1 and P acupuncture sites.

FIG. 3 illustrates exemplary acupuncture sites 104. Acupuncture sites, P1 and P2, are located at opposing sides of the thyroid cartilage in the anterior region of the neck adjacent to acupuncture site RN 23 (LIAN QUAN). Stimulation at P1 and P2 is believed to be beneficial to blood pressure and related cardiac parameters and, accordingly, P1 and P2 are generally referred to in the figure as cardiac and blood pressure sites. Stimulation at these sites may be particularly beneficial to hypertension. Acupuncture sites, L1 and L2 are located along the sternum at the clavicle (L1) and between rib one and rib two (L2) with L1 corresponding to site RN 22 (TIAN TU) and L2 corresponding to site RN 20 (HUA GAD. Stimulation at L1 and L2 is believed to be beneficial to respiration and, accordingly, L1 and L2 are generally referred to in the figure as lung and throat sites. Stimulation at these sites may be particularly beneficial to respiratory problems such as CSR and sleep apnea. Three additional sites, H1, H2+ and H2−, are located along sternum between rib two and rib three (H1) and at two sites below the rib cage H2+ and H2−) with H1 corresponding to site RN 19 (ZI GONG), H2+ corresponding to site RN 15 (JIU WEI) and H2− corresponding to site RN 14 (JU JUE.) Stimulation at H1, H2+ and H2− is believed to be particularly beneficial to cardiac health and, accordingly, these sites are generally referred to in the figure as cardiac sites. Stimulation at these sites may be particularly beneficial to cardiac problems such as heart failure and arrhythmia. Additionally within the figure, for the sake of completeness, other acupuncture sites are identified by their Chinese characters. Some of these may be pertinent to other medical conditions, such as kidney problems or diabetes, discussed below.

Returning again to FIG. 2, at step 106, the CRMD records diagnostic information representative of the health of the patient and the efficacy of neurostimulation and then returns to step 100 to detect updated parameters. In this manner, neurostimulation may be adaptively varied in a feedback loop to determine preferred or optimal stimulation parameters for addressing health conditions or for responding to new conditions that might arise. Note that, insofar as the terms thorax, neck and abdomen are concerned, herein, the thorax is regarded as the region of the chest from the thoracic inlet to the thoracic diaphragm, with the neck beginning above the thoracic inlet and the abdomen beginning below the thoracic diaphragm and extending to the pelvic inlet.

Exemplary Acupuncture Site Neurostimulation Control Techniques

Figure 4:
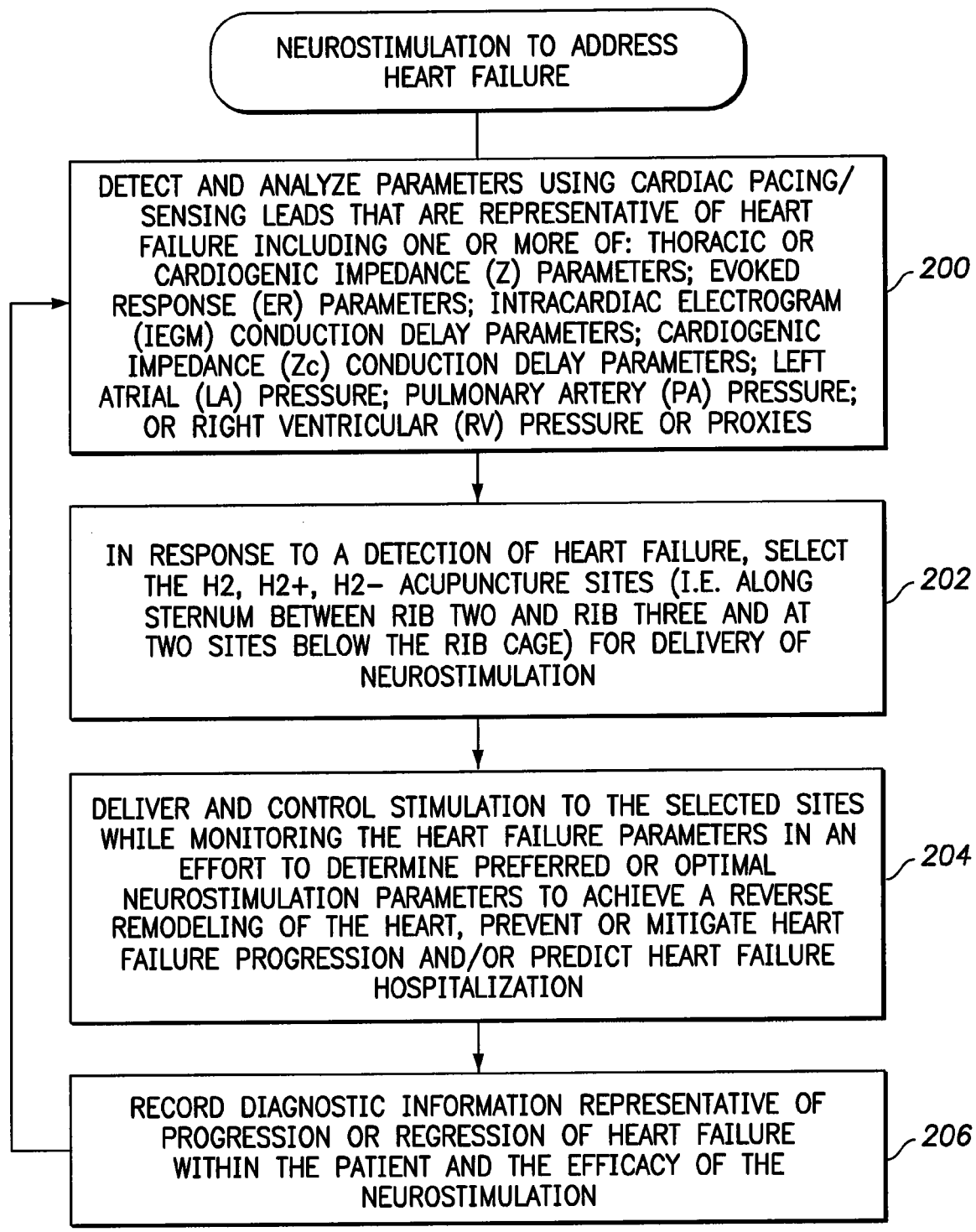
FIG. 4 is an exemplary embodiment of the general neurostimulation technique of FIG. 2 for use with heart failure.

FIG. 4 illustrates techniques for detecting heart failure and delivering neurostimulation in response thereto at the H2, H2+, H2− acupuncture sites. At step 200, the CRMD detects parameters using cardiac pacing/sensing leads that are representative of heart failure including one or more of: thoracic impedance (Z) or cardiogenic impedance (Zc) parameters; ER parameters; IEGM conduction delay parameters; cardiogenic impedance (Zc) conduction delay parameters; left atrial (LA) pressure; pulmonary artery (PA) pressure; or right ventricular (RV) pressure (if suitable pressure sensors or proxies are available.)

Thoracic impedance may be detected between an electrodes implanted on or in the heart of the patient and the device housing (or can) of the CRMD, such as along a vector between the LV tip and the device can. Thoracic impedance is discussed, for example, in U.S. Published Patent Application 2008/0091114 of Min et al., entitled "Techniques for Correlating Thoracic Impedance with Physiological Status", now abandoned. Cardiogenic impedance may be detected between a pair of electrodes implanted on or in the heart of the patient, such as along a vector between the LV tip and RV tip electrodes. Cardiogenic impedance is discussed, for example, in U.S. Pat. No. 8,050,760 to Cholette, entitled "System and Method for Evaluating Mechanical Cardiac Dyssynchrony based on Multiple Impedance Vectors using an Implantable Medical Device." ERs may be detected within the IEGM and are discussed, for example, in U.S. Pat. No. 8,090,444 of Min et al., entitled "Optimization of Cardiac Pacing Therapy based on Paced Propagation Delay." IEGM conduction delay parameters include parameters such as atrioventricular delays (AV/PV) and interventricular delays (VV) detected, for example, by comparing the timing of P-waves and R-waves in various IEGM signals. IEGM conduction delays are discussed, for example, in U.S. Pat. No. 7,248,925 to Bruhns et al., entitled "System and Method for Determining Optimal Atrioventricular Delay based on Intrinsic Conduction Delays." Zc-based conduction delays also include parameters such as VV (but derived from Zc rather than the IEGM.) Zc-based conduction delays are discussed, for example, in U.S. Pat. No. 8,208,999 of Wenzel et al., entitled "System and Method for Estimating Electrical Conduction Delays from Immittance Values Measured Using an Implantable Medical Device." Ventricular conduction delays are discussed in pending U.S. Published Patent Application 2011/0137369 of Ryu et al., entitled "Optimal Pacing Configuration via Ventricular Conduction Delays." See, also pending U.S. Published Patent Application 2012/0136406 of Min et al., entitled "Systems and Methods for Determining Optimal Atrioventricular Pacing Delays based on Cardiomechanical Delays."

At step 200, the CRMD also analyzes the parameters to detect an indication of heart failure. For example, certain changes within thoracic or cardiogenic impedance parameters (or conduction delays derived therefrom) may indicate the onset or progression of heart failure (based on a comparison against suitable threshold values.) See, for example, the aforementioned patent to Cholette (U.S. Pat. No. 8,050,760), which exploits cardiogenic impedance. See, also, U.S. Pat. No. 8,032,212 to Bornzin et al., entitled "System and Method for Monitoring Thoracic Fluid Levels based on Impedance using an Implantable Medical Device," which discusses the use of long-term trends within thoracic impedance to detect heart failure. Likewise, certain changes within the ER may indicate the onset or progression of heart failure. See, for example, U.S. Pat. No. 7,440,804 to Min et al., entitled "System and Method for Measuring Ventricular Evoked Response using an Implantable Medical Device", U.S. Pat. No. 7,430, 447 to Min et al., entitled "Evoked Response and Impedance Measures for Monitoring Heart Failure and Respiration" and U.S. Pat. No. 6,473,647 to Bradley, entitled "Implantable Cardiac Stimulation Device for and Method of Monitoring Progression or Regression of Heart Disease by Monitoring Evoked Response Features."

At step 202, in response to a detection of heart failure, the CRMD selects the H2, H2+, H2− acupuncture sites (i.e. the sites along sternum between rib two and rib three and at two sites below the rib cage) for delivery of neurostimulation. For example, if the CRMD is coupled to a neurostimulation lead that includes stimulation electrodes at each of the H1, H2+, H2−, L1, L2, P1 and P2 sites, the CRMD engages switching components at step 202 to connect the electrodes at H1, H2+, H2− to a stimulation pulse generator within the CRMD so that neurostimulation pulses may be delivered to H1, H2+ and H2−(or some subset thereof.) At step 204, the CRMD delivers and controls stimulation to the selected sites while monitoring heart failure parameters in an effort to determine preferred or optimal neurostimulation parameters to achieve a reverse remodeling of the heart, prevent or mitigate heart failure progression and/or predict a heart failure hospitalization. At step 206, the CRMD records diagnostic information representative of the progression or regression of heart failure within the patient and the efficacy of the neurostimulation. As shown, steps 200-206 may be repeated in a closed loop so that the device can periodically assess whether the neurostimulation is having a beneficial effect on the patient by examining the parameters indicative of heart failure. The various neurostimulation control parameters (including pulse frequency, pulse width, pulse amplitude, pulse pattern, pulse configuration and the particular sites to be stimulated) can be adaptively adjusted during each iteration to identify the preferred or optimal set of parameters to achieve a beneficial effect on the patient. (See, FIG. 12, discussed below, for further information on the neurostimulation control parameters and the various configurations that might be employed.) It should be understood that "optimal" neurostimulation parameters obtained using techniques described herein are not necessarily absolutely optimal in a given quantifiable or mathematical sense. What constitutes "optimal" depends on the criteria used for judging the resulting performance, which can be subjective in the minds of patients and clinicians. The neurostimulation control parameters identified or selected using the techniques described herein represent, at least, a "preferred" set of neurostimulation control parameters. Clinicians (or in some case patients) may choose to adjust or alter the neurostimulation control parameters at their discretion using suitable external control devices.

Figure 5:
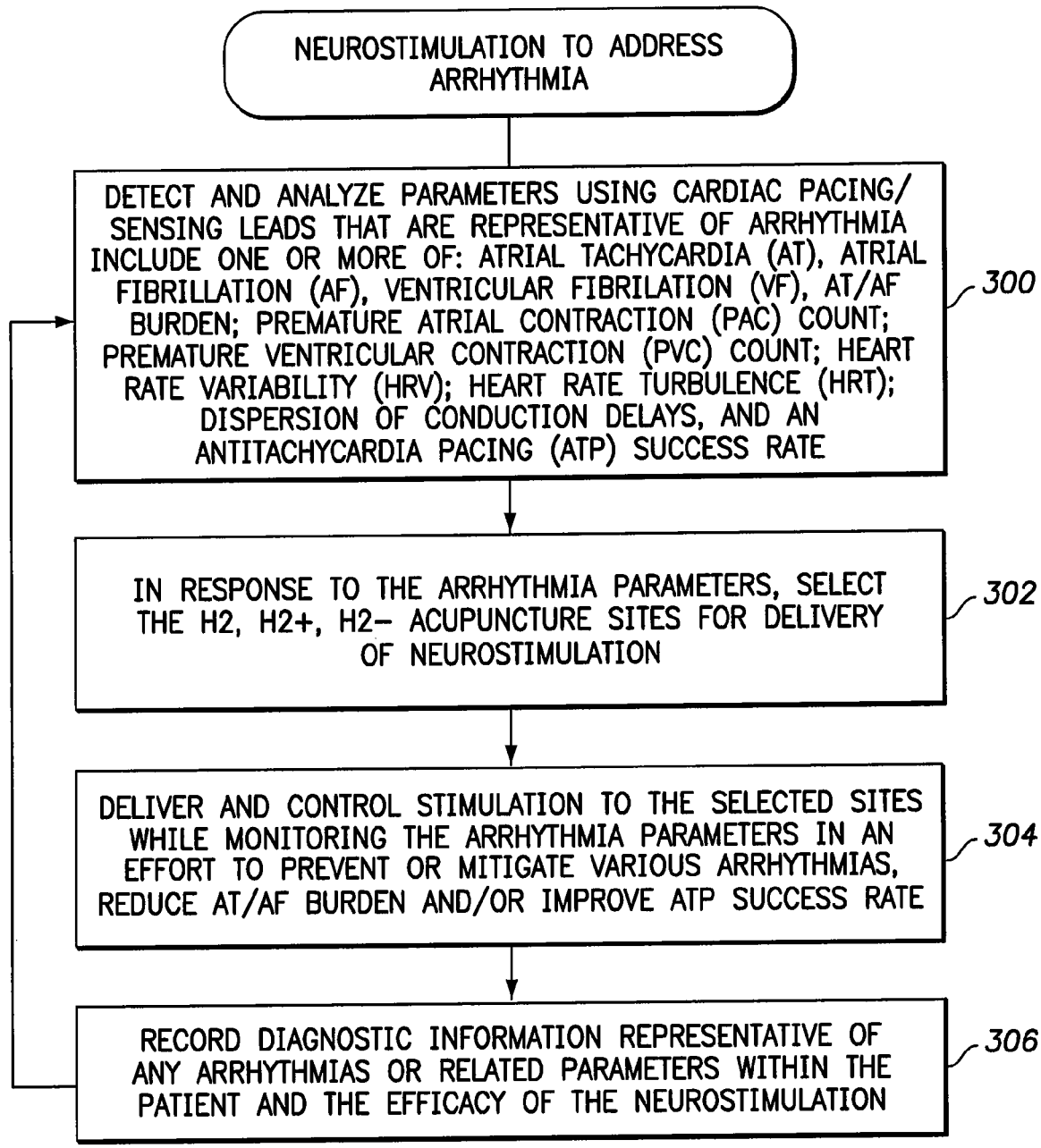
FIG. 5 is an exemplary embodiment of the general neurostimulation technique of FIG. 2 for use with arrhythmia.

FIG. 5 illustrates techniques for detecting arrhythmias and related conditions and for delivering neurostimulation in response thereto at the H2, H2+, H2− acupuncture sites. At step 300, the CRMD detects and analyzes parameters using cardiac pacing/sensing leads that are representative of arrhythmia include one or more of: AT, AF, VF, AT/AF burden; PAC count; PVC count; HRV; HRT; dispersion of conduction delays and ATP success rate. Briefly, the AT/AF burden is a quantized parameter indicating the intensity or amount of observed AT/AF within the patient. The AT/AF burden is discussed, for example, in U.S. Pat. No. 7,606,618 to Bornzin et al., entitled "Implantable medical device with notification system." In some examples, AT/AF burden is calculated as the fraction of time in auto mode switch out of the total time not tachypacing to induce AF. In other examples, mean AT/AF times are used to assess the AT/AF burden, wherein the mean AT/AF time is representative of the total duration of spontaneous AT/AF episodes in the patient divided by the corresponding follow-up time. That is, during device operation, the device detects and tracks episodes of AT and AF and assesses the accumulated duration or time of individual episodes relative to corresponding follow-up times so as to assess the mean AT/AF time. The mean AT/AF time can be represented by days from the start of the follow-up.

PACs and PVCs may be detected and counted within atrial and ventricular IEGM signals, respectively. See, for example, U.S. Pat. No. 5,908,392 to Wilson et al., entitled "System and Method for Recording and Storing Medical Data in Response to a Programmable Trigger" and U.S. Pat. No. 8,019,417 to Bornzin et al., entitled "PAC therapy." HRV is a physiological phenomenon where the time interval between heartbeats varies and is typically measured as the variation in the beat-to-beat interval. Other terms for HRV may include: "cycle length variability," "RR variability" (where RR is the interval between successive peaks of QRS complexes in the IEGM), and "heart period variability." HRV is discussed in pending U.S. Published Patent Application 2009/0264783 to Xi et al., entitled "Systems and Methods for Improved Atrial Fibrillation (AF) Monitoring" and U.S. Pat. No. 6,480,733 to Turcott, entitled "Method for Monitoring Heart Failure." HRT refers to a return to equilibrium of heart rate after a PVC. HRT is discussed in U.S. Pat. No. 7,869,870 to Farazi, entitled "System and Method of using Vagal Stimulation to assess Autonomic Tone and Risk of Sudden Cardiac Death in an Implantable Cardiac Device." ATP success rate refers to the percentage of episodes of an arrhythmia that are terminated by ATP (usually with reference to episodes of AT/AF.) ATP is discussed in U.S. Pat. No. 7,295,873 to Min et al., entitled "Anti-tachycardia Pacing Method and Apparatus for Multi-Chamber Pacing" and in U.S. Pat. No. 7,826,899 to Ryu et al., entitled "Neurostimulation and Neurosensing Techniques to Optimize Atrial Anti-Tachycardia Pacing for Termination of Atrial Tachyarrhythmias."

At step 302, in response to the arrhythmia parameters, the CRMD selects the H2, H2+, H2− acupuncture sites (or some subset thereof) for delivery of neurostimulation. For example, if the counts of PACs or PVCs increase above a pre-determined value over consecutive days, neurostimulation is activated. Similarly, for HRV or HRT, if an amount of decrease in HRV exceeds a pre-determined value over consecutive days, neurostimulation is activated. For AT/AF burden, if the AT/AF burden increases over several days consecutively, neurostimulation is activated. Dispersion of conduction delays may be calculated from the IEGM. If the standard deviation in the dispersion is greater than a pre-determined value, neurostimulation is activated.

At step 304, the CRMD delivers and controls stimulation to the selected sites while monitoring the arrhythmia parameters in an effort to determine preferred or optimal neurostimulation parameters to prevent or mitigate the detected arrhythmia, reduce the AT/AF burden and/or improve the ATP success rate. For ATP, when AF is detected, neurostimulation at cardiac-based acupuncture sites (excluding those pertaining to blood pressure) can be enabled in combination of AF suppression algorithms of the CRMD to increase the chance of AF termination. Prior to (or during) ATP for VT or atrial flutter, neurostimulation can also be activated.

At step 306, the CRMD records diagnostic information representative of the progression or regression of any arrhythmias or related conditions within the patient and the efficacy of the neurostimulation. As shown, steps 300-306 may be repeated in a closed loop so that the device can periodically assess whether the neurostimulation is having a beneficial effect on the patient by examining the parameters indicative of arrhythmia. The various neurostimulation control parameters can be adaptively adjusted during each iteration to identify the preferred or optimal set of parameters to achieve a beneficial effect on the patient. (Again see, FIG. 12, discussed below.)

Figure 6:
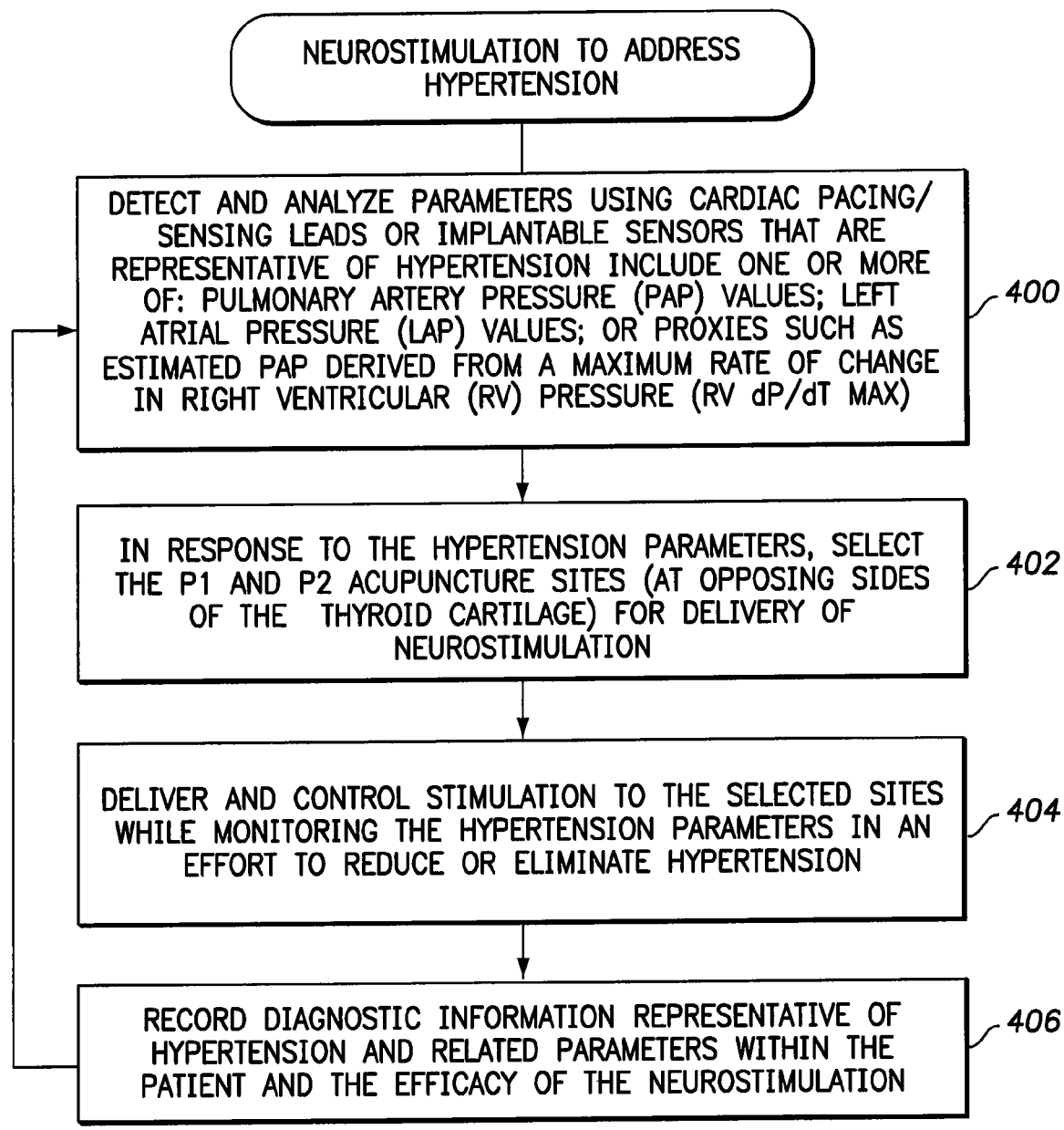
FIG. 6 is an exemplary embodiment of the general neurostimulation technique of FIG. 2 for use with hypertension.

FIG. 6 illustrates techniques for detecting hypertension and related conditions and delivering neurostimulation in response thereto at the P1 and P2 acupuncture sites. At step 400, the CRMD detects and analyzes parameters using cardiac pacing/sensing leads and/or implantable sensors that are representative of hypertension include one or more of: PAP; LAP; or suitable proxies such as estimated PAP derived from a maximum rate of change in RV pressure (i.e. RV dP/dt max.) A CardioMEMS™ or similar device may be used to assess some of these parameters and may, for example, be implanted in the RV. See, for example, U.S. Pat. No. 7,621,036 of Cros et al., entitled "Method of Manufacturing Implantable Wireless Sensor for In Vivo Pressure Measurement," pending U.S. Patent Application 2006/0287602 of O'Brien et al., entitled "Implantable Wireless Sensor for In Vivo Pressure Measurement," and U.S. Pat. No. 8,021,307 to White et al., entitled "Apparatus and Method for Sensor Deployment and Fixation," each initially assigned to CardioMems, Inc. PAP is discussed in U.S. Published Patent Application 2008/0288013 (now abandoned) of Schecter, entitled "Pulmonary Pressure Monitoring." LAP is discussed in U.S. Pat. No. 7,794,404 to Gutfinger et al., entitled "System and Method for Estimating Cardiac Pressure using Parameters derived from Impedance Signals detected by an Implantable Medical Device" and pending U.S. Patent Application 2011/0208077 to Soriano et al., entitled "System and Method for Exploiting Atrial Electrocardiac Parameters in Assessing Left Atrial Pressure using an Implantable Medical Device." See, also U.S. Pat. No. 8,147,416 of Fayram et al., entitled "Implantable Systemic Blood Pressure Measurement Systems and Methods."

At step 402, in response to the hypertension parameters, the CRMD selects the P1 and P2 acupuncture sites (or just one of the sites) for delivery of neurostimulation. At step 404, the CRMD delivers and controls stimulation to the selected sites while monitoring the arrhythmia parameters in an effort to determine preferred or optimal neurostimulation parameters to reduce or mitigate hypertension. This may be achieved, in part, by averaging PAP or LAP pressure signals over several heart beats (respiration cycles) to determine whether the signals are generally increasing. When PAP or LAP pressures are indicated to be increasing, the acupuncture sites for cardiac and blood pressures are stimulated for a programmed period of time and the effect on pressures is observed for a programmed number of days. If no significant effect is detected, the intervention is halted, warning signals are relayed to the clinician and other therapies such as medications are initiated. At step 406, the CRMD records diagnostic information representative of hypertension or related conditions within the patient and the efficacy of the neurostimulation. Steps 400-406 may be repeated in a closed loop so that the device can periodically assess whether the neurostimulation is having a beneficial effect on the patient by examining the parameters indicative of hypertension. The various neurostimulation control parameters can be adaptively adjusted during each iteration to identify the preferred or optimal set of parameters to achieve a beneficial effect on the patient. (Again see, FIG. 12, discussed below.)

Figure 7:
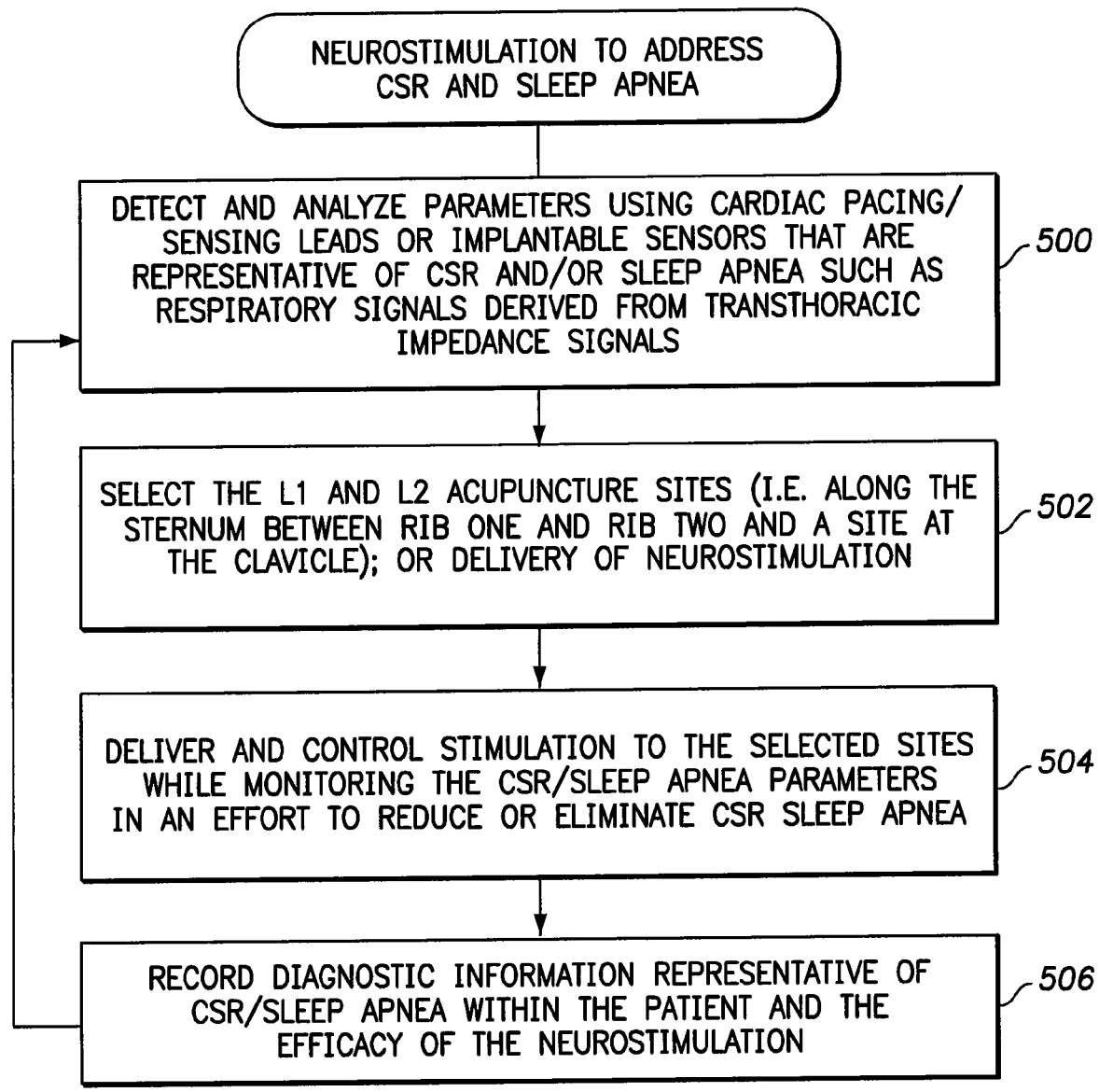
FIG. 7 is an exemplary embodiment of the general neurostimulation technique of FIG. 2 for use with CSR and/or sleep apnea.

FIG. 7. illustrates techniques for detecting CSR, sleep apnea and related conditions and for delivering neurostimulation in response thereto at the L1 and L2 acupuncture sites. At step 500, the CRMD detects and analyzes parameters using cardiac pacing/sensing leads and/or implantable sensors that are representative of CSR and/or sleep apnea including respiratory signals derived from a transthoracic impedance signal. See, for example, pending U.S. Published Patent Application 2011/0184304 of Koh, entitled "Implantable Medical Device with Sleep Apnea Detection Control and Method" and U.S. Pat. No. 7,357,775 of Koh, entitled "System and Method for Providing Demand-Based Cheyne-Stokes Respiration Therapy using an Implantable Medical Device." At step 502, in response to the CSR or sleep apnea parameters, the CRMD selects the L1 and L2 acupuncture sites (or just one of the sites) for delivery of neurostimulation. At step 504, the CRMD delivers and controls stimulation to the selected sites while monitoring the CSR/sleep apnea parameters in an effort to determine preferred or optimal neurostimulation parameters to reduce or mitigate CSR and/or sleep apnea. At step 506, the CRMD records diagnostic information representative of CSR/sleep apnea or related conditions within the patient and the efficacy of the neurostimulation. Steps 500-506 may be repeated in a closed loop so that the device can periodically assess whether the neurostimulation is having a beneficial effect on the patient by examining the parameters indicative of CSR/sleep apnea. The various neurostimulation control parameters can be adaptively adjusted during each iteration to identify the preferred or optimal set of parameters to achieve a beneficial effect on the patient. (Again see, FIG. 12, discussed below.)

Figure 8:
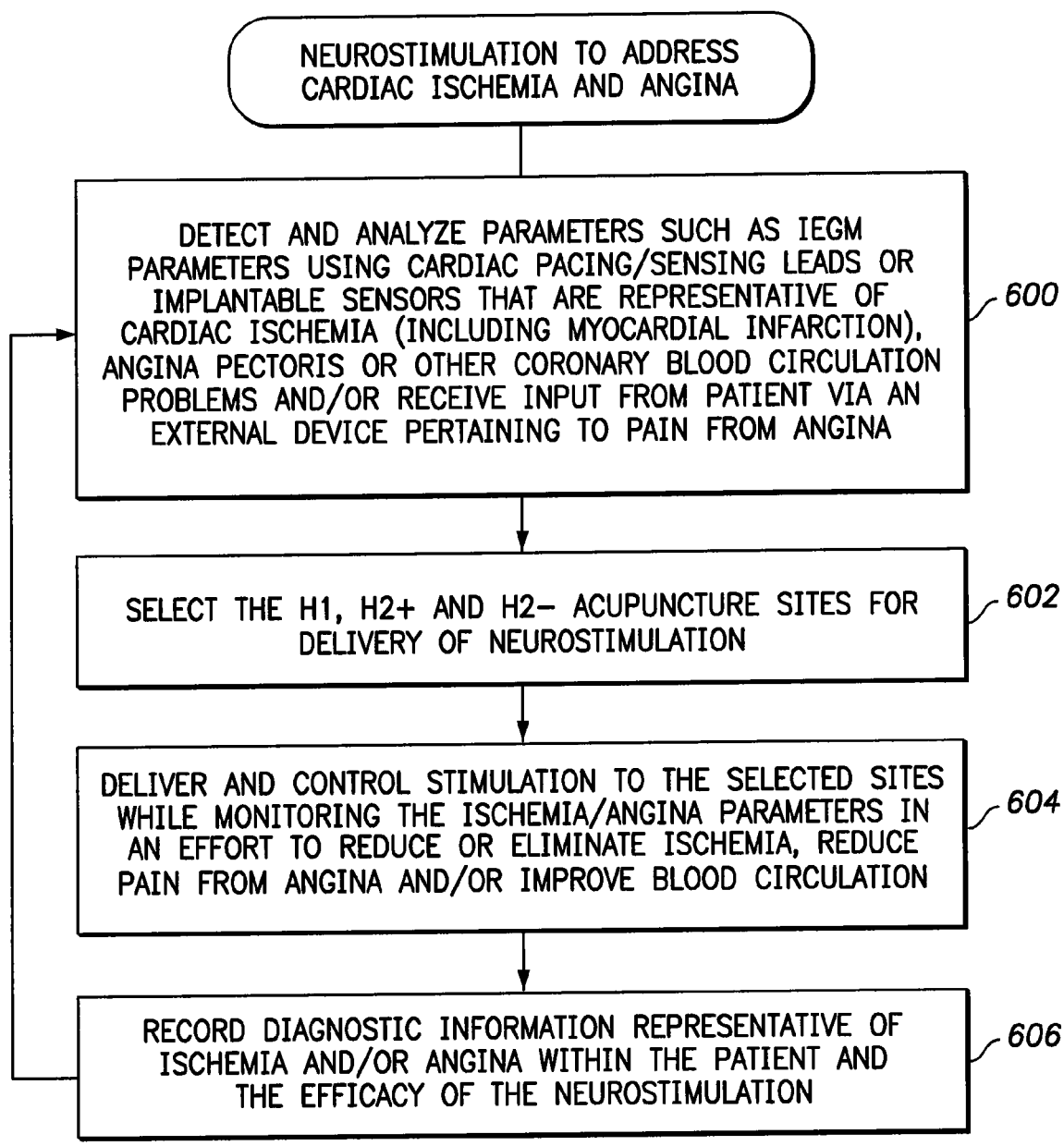
FIG. 8 is an exemplary embodiment of the general neurostimulation technique of FIG. 2 for use with ischemia and/or angina or other coronary blood circulation problems.

FIG. 8 illustrates techniques for detecting cardiac ischemia (including myocardial infarction), angina pectoris and related conditions and for delivering neurostimulation in response thereto at the H1, H2+ and H2− acupuncture sites. At step 600, the CRMD detects and analyzes parameters (including pertinent IEGM signals) using cardiac pacing/sensing leads and/or implantable sensors that are representative of ischemia, angina or other coronary blood circulation problems. See, for example, U.S. Pat. No. 8,090,435 to Gill et al., entitled "System and Method for Distinguishing among Cardiac Ischemia, Hypoglycemia and Hyperglycemia using an Implantable Medical Device" and U.S. Pat. No. 8,162,842 of Gill et al., entitled "Detecting Ischemia using an Implantable Cardiac Device Based on Morphology of Cardiac Pressure Signal". Angina is discussed in U.S. Published Patent Application 2009/0099467 of Toren-Herrinton et al., entitled "Method and System for Tracking Quality of Life in Patients with Angina." At step 600, the device can also receive or input from the patient or caregiver from an external device pertaining to pain from angina. For example, the patient may use a PAM or bedside monitor to enter information pertaining to angina pain, which is then transmitted to the implantable device.

At step 602, in response to ischemia, angina or related conditions, the CRMD selects the H1, H2+ and H2− acupuncture sites (or a subset thereof) for delivery of neurostimulation. At step 604, the CRMD delivers and controls stimulation to the selected sites while monitoring the ischemia/angina parameters in an effort to determine preferred or optimal neurostimulation parameters to reduce or mitigate ischemia and pain from angina and/or improve blood circulation. At step 606, the CRMD records diagnostic information representative of ischemia/angina or related conditions within the patient and the efficacy of the neurostimulation. Steps 600-606 may be repeated in a closed loop so that the device can periodically assess whether the neurostimulation is having a beneficial effect on the patient by examining the parameters indicative of ischemia/angina. The various neurostimulation control parameters can be adaptively adjusted during each iteration to identify the preferred or optimal set of parameters to achieve a beneficial effect on the patient. (Again see, FIG. 12, discussed below.)

Figure 9:
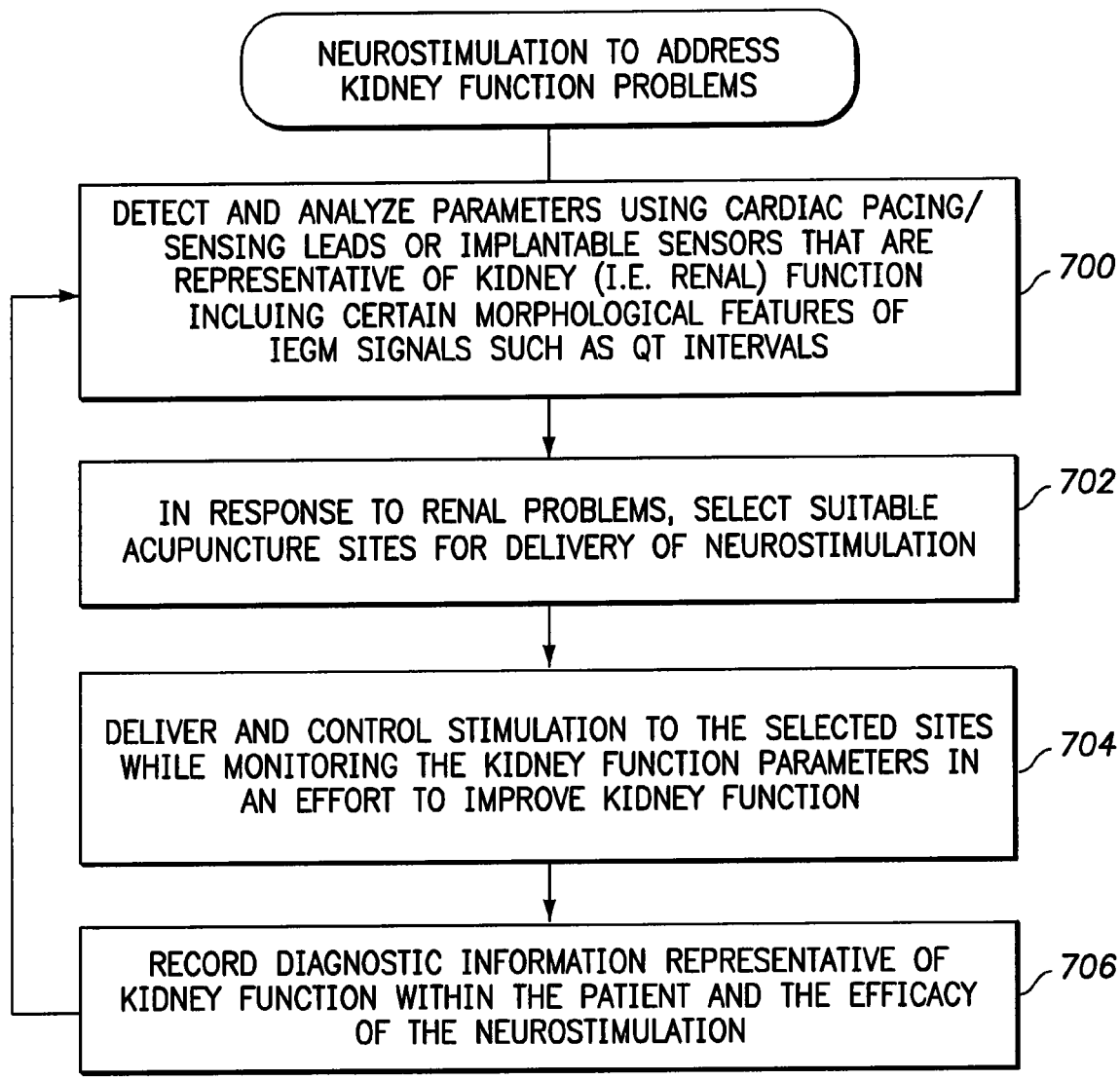
FIG. 9 is an exemplary embodiment of the general neurostimulation technique of FIG. 2 for use in connections with kidney function.

FIG. 9 illustrates techniques for detecting kidney problems and related conditions and for delivering neurostimulation in response thereto at suitable acupuncture sites (which typically requires placement of neurostimulation leads at locations other than those specifically discussed above.) At step 700, the CRMD detects and analyzes parameters using cardiac pacing/sensing leads and/or implantable sensors that are representative of kidney function (i.e. renal function) including pertinent IEGM signals. Techniques for detecting renal failure based on IEGM signals are discussed in U.S. Pat. Nos. 7,529,580 and 7,400,920, entitled "Detection of Renal Failure by Cardiac Implantable Medical Device." Briefly, as described therein, morphological features within electrical cardiac signals are tracked and changes are monitored to detect renal failure. The morphological feature may be an interval between corresponding polarization events such as the interval between QRS-complexes and peaks of corresponding T-waves (QTmax interval); the interval between QRS-complexes and ends of corresponding T-waves (QTend interval); or the interval between P-waves and corresponding QRS-complexes (PR interval). See, also, U.S. Pat. No. 7,953,479 to Wenzel et al., entitled "Acquiring Nerve Activity from Carotid Body and/or Sinus," which notes that a relationship between carotid sinus nerve activity and blood potassium concentration may be used to diagnose renal condition.

At step 702, in response to an indication of kidney problems or related conditions, the CRMD selects suitable acupuncture sites for delivery of neurostimulation. At step 704, the CRMD delivers and controls stimulation to the selected sites while monitoring the kidney function parameters in an effort to determine preferred or optimal neurostimulation parameters to address the kidney function parameters. See, also, U.S. Published Patent Application 2003/0216792 of Levin et al., entitled "Renal Nerve Stimulation Method and Apparatus for Treatment of Patients" (now U.S. Pat. No. 7,162,303, issued Jan. 9, 2007). At step 706, the CRMD records diagnostic information representative of kidney function problems or related conditions within the patient and the efficacy of the neurostimulation. Steps 700-706 may be repeated in a closed loop so that the device can periodically assess whether the neurostimulation is having a beneficial effect on the patient by examining the parameters indicative of kidney function. The various neurostimulation control parameters can be adaptively adjusted during each iteration to identify the preferred or optimal set of parameters to achieve a beneficial effect on the patient. (Again see, FIG. 12, discussed below.)

Figure 10:
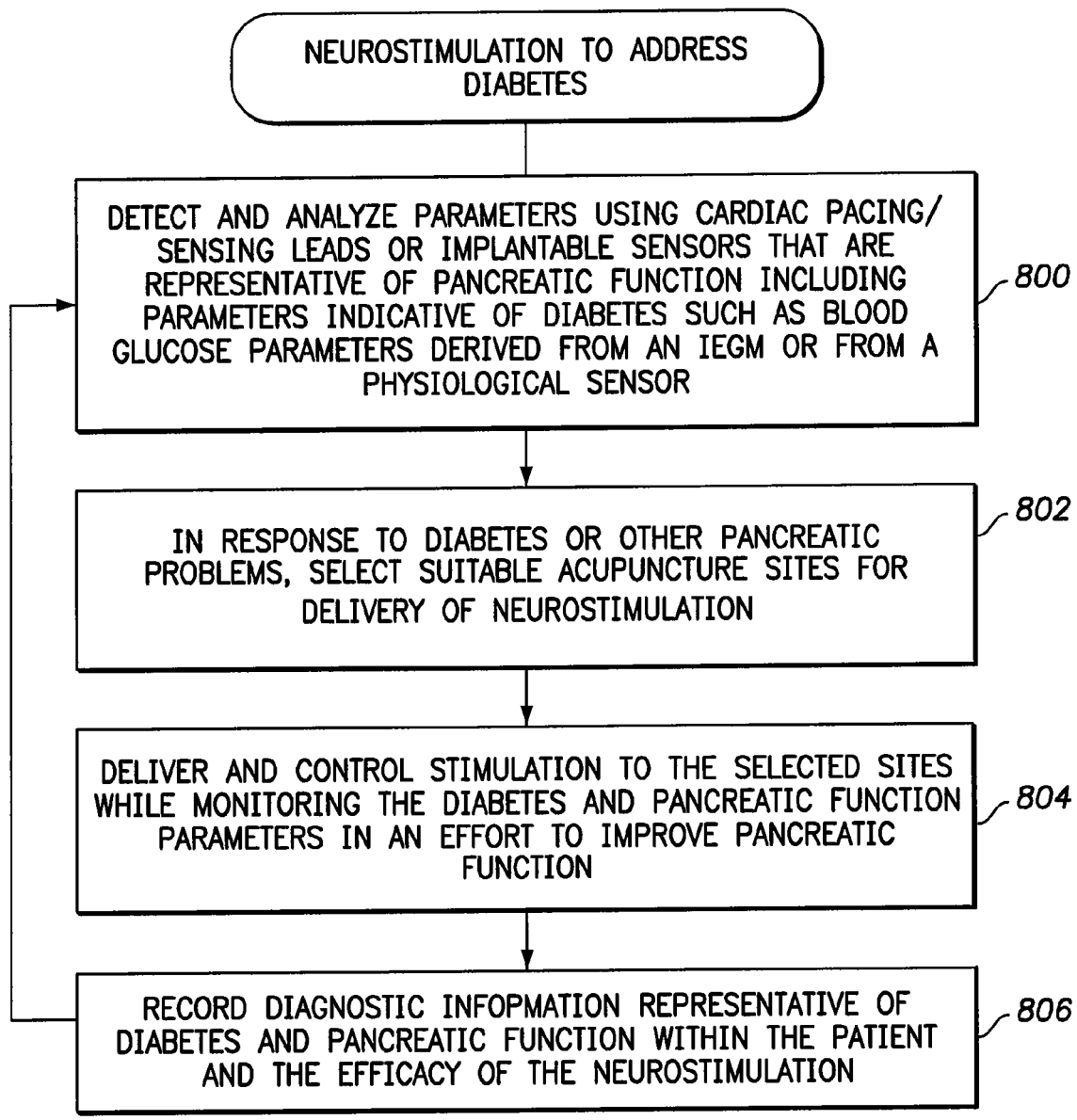
FIG. 10 is an exemplary embodiment of the general neurostimulation technique of FIG. 2 for use with diabetes.

FIG. 10 illustrates techniques for detecting diabetes and related pancreatic conditions and for delivering neurostimulation in response thereto at suitable acupuncture sites (which typically requires placement of neurostimulation leads at locations other than those specifically discussed above.). At step 800, the CRMD detects and analyzes parameters using cardiac pacing/sensing leads and/or implantable sensors that are representative of diabetes (or other pancreatic function issues) including pertinent IEGM signals indicative of blood glucose levels. See, for example, U.S. Pat. No. 7,462,150 to Bharmi, entitled "System and Method for Evaluating Impaired Glucose Tolerance and Diabetes Mellitus within a Patient using an Implantable Medical Device" and U.S. Pat. No. 7,103,412 to Kroll, entitled "Implantable Cardiac Stimulation Device and Method for Detecting Asymptomatic Diabetes." See, also, U.S. Pat. No. 8,090,435 to Gill et al., entitled "System and Method for Distinguishing among Cardiac Ischemia, Hypoglycemia and Hyperglycemia using an Implantable Medical Device" and related U.S. Pat. Nos. 7,756,572; 7,502,644; 7,297,114; and 7,272,436. See, also, U.S. Pat. No. 8,092,386 to Wenzel et al., entitled "Method and Implantable System for Blood-Glucose Concentration Monitoring."

At step 802, in response to an indicative of diabetes or pancreatic problems or related conditions, the CRMD selects the suitable acupuncture sites for delivery of neurostimulation. At step 804, the CRMD delivers and controls stimulation to the selected sites while monitoring the diabetes/pancreatic function parameters in an effort to determine preferred or optimal neurostimulation parameters to address the diabetes/pancreatic problems. See, also, U.S. Published Patent Application 2010/0057158 of Rodriguez et al., entitled "Neurostimulation based on Glycemic Condition" (now abandoned). At step 806, the CRMD records diagnostic information representative of diabetes/pancreatic function problems or related conditions within the patient and the efficacy of the neurostimulation. Steps 800-806 may be repeated in a closed loop so that the device can periodically assess whether the neurostimulation is having a beneficial effect on the patient by examining the parameters indicative of diabetes. The various neurostimulation control parameters can be adaptively adjusted during each iteration to identify the preferred or optimal set of parameters to achieve a beneficial effect on the patient. (Again see, FIG. 12, discussed below.)

Figure 11:
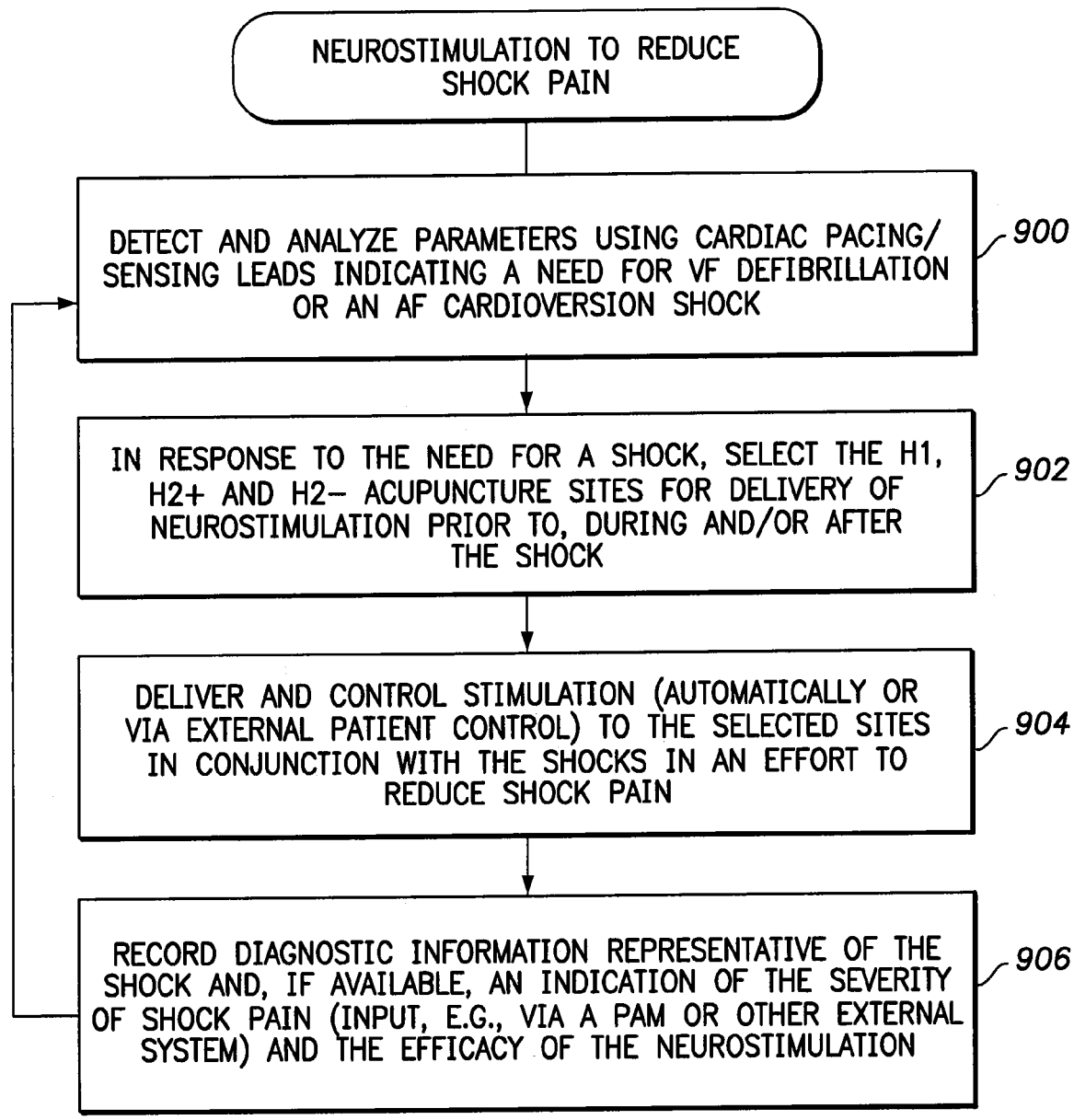
FIG. 11 is an exemplary embodiment of the general neurostimulation technique of FIG. 2 for use in reducing shock pain.

FIG. 11 illustrates techniques for delivering neurostimulation at the H1, H2+ and H2− acupuncture sites to reduce pain associated with shocks. At step 900, the CRMD detects and analyzes parameters using cardiac pacing/sensing leads indicating the need for a VF defibrillation shock or an AF cardioversion shock. For example, the atrial or ventricular rate may be detected and compared against a rate threshold indicative of fibrillation. See, also, techniques described in U.S. Patent Application 2007/0156056 of Min et al., entitled "System and Method for Detecting Cardiac Ischemia Based on T-Waves using an Implantable Medical Device" (now U.S. Pat. No. 7,643,872, issued Jan. 5, 2010), and U.S. Pat. No. 5,623,936 to McClure, entitled "Implantable Medical Device having Means for Discriminating between True R-waves and Ventricular Fibrillation." At step 902, in response to the need for shock, the CRMD selects the H1, H2+ and H2− acupuncture sites (or a subset thereof) for delivery of neurostimulation prior to, during and/or after the shock.

At step 904, the CRMD delivers and controls neurostimulation (automatically or via external patient control) to the selected sites in conjunction with the shocks in an effort to reduce shock pain. For example, when the device detects AF and attempts at ATP or AF suppression fail, AF high voltage (HV) shocks may be delivered. Prior to and during a shock, stimulation to H1, H2+ and H2− can be delivered to reduce shock induced pain either automatically or activated by a patient. Likewise, prior and during a HV ventricular defibrillation shock, stimulation to H1, H2+ and H2− will be delivered to reduce shock induced pain. Therapy can be enabled directly by the CRM device, upon initial detection of tachyarrhythmia, and maintained until a specified time after return to sinus rhythm. Stimulation pulse trains may be used. Insofar as patient activation is concerned, in some examples, if an AF cardioversion shock is needed, the patient is warned (via a PAM) and then given an opportunity to activate neurostimulation prior to the shock. In other examples, the neurostimulation would be automatic. See, also, the aforementioned patent entitled "Pacing Therapy and Acupuncture" (U.S. Pat. No. 7,321,792 to Min et al.) See, also, U.S. Pat. No. 7,113,822 to Kroll, entitled "System and Method for Providing Cardioversion Therapy and Overdrive Pacing using an Implantable Cardiac Stimulation Device" and U.S. Pat. No. 7,164,944 to Kroll et al., entitled "Analgesic Therapy for ICD Patients."

At step 906, the CRMD records diagnostic information representative of the shock and, if available, information indicative of the severity of the shock pain and the efficacy of the neurostimulation. For example, after a shock, the patient may be invited to rank the severity of the shock pain (via a PAM or other external device) so that adjustments can be made, if needed, to subsequent neurostimulation in an effort to further reduce shock pain. Steps 900-906 may be repeated in a closed loop so that the device can periodically assess whether the neurostimulation is having a beneficial effect on the patient by examining the parameters indicative of shock pain. The various neurostimulation control parameters can be adaptively adjusted during each iteration to identify the preferred or optimal set of parameters to achieve a beneficial effect on the patient. (Again see, FIG. 12.)

FIG. 12 illustrates techniques generally applicable to the foregoing neurostimulation techniques for use in selecting a particular lead location and/or configuration. At step 1000, in response to the need for neurostimulation, the CRMD selects stimulation electrodes based on the location of the acupuncture site where stimulation is needed (as described above in FIGS. 4-11) from among various lead arrangements that may include: percutaneous leads having three pairs of bipolar electrodes, with each pair at a different site; two sternum (STN) leads with one implanted subcutaneously and the other implanted under the sternum and stimulated using all cathodes on one lead and all anodes on the other; sternum (STN) leads implanted in pectoral regions of the patient (either left or right pectoral regions); and sternum (STN) leads implanted in abdominal regions of the patient (either left or right abdominal regions). Typically, for a given acupuncture site (such as L1), there will only be one set of electrodes available at that location but if a choice is available, the CRMD makes the choice at step 1000 from among candidate electrodes. Exemplary lead configurations will be further described with reference to FIGS. 13-19.

At step 1002, the CRMD then delivers and controls stimulation to H1, H2+, H2−, L1, L2, P1 and P2 sites (and additional possible sites such as T1-T5, T11-L2, discussed below) using the selected lead arrangement using: a simultaneous stimulation pattern; a sequential stimulation pattern; or a combination of simultaneous and sequential stimulation patterns. The pulse frequencies may be in the range of 20-50 Hz. A pulse width of about 0.2 ms and a maximum voltage of about 13.5 V may be used. As already noted, the stimulation control parameters (including the location of the stimulation) may be adaptively adjusting or changed by the CRMD by an amount sufficient to improve at least one parameter representative of the health of the patient. For example, after a period of time during which neurostimulation is delivered, the CRMD can assess the efficacy of the stimulation and then automatically adjust the parameters in an effort to improve the efficacy of the stimulation.

Exemplary Neurostimulation Lead and Configurations

Figure 13:
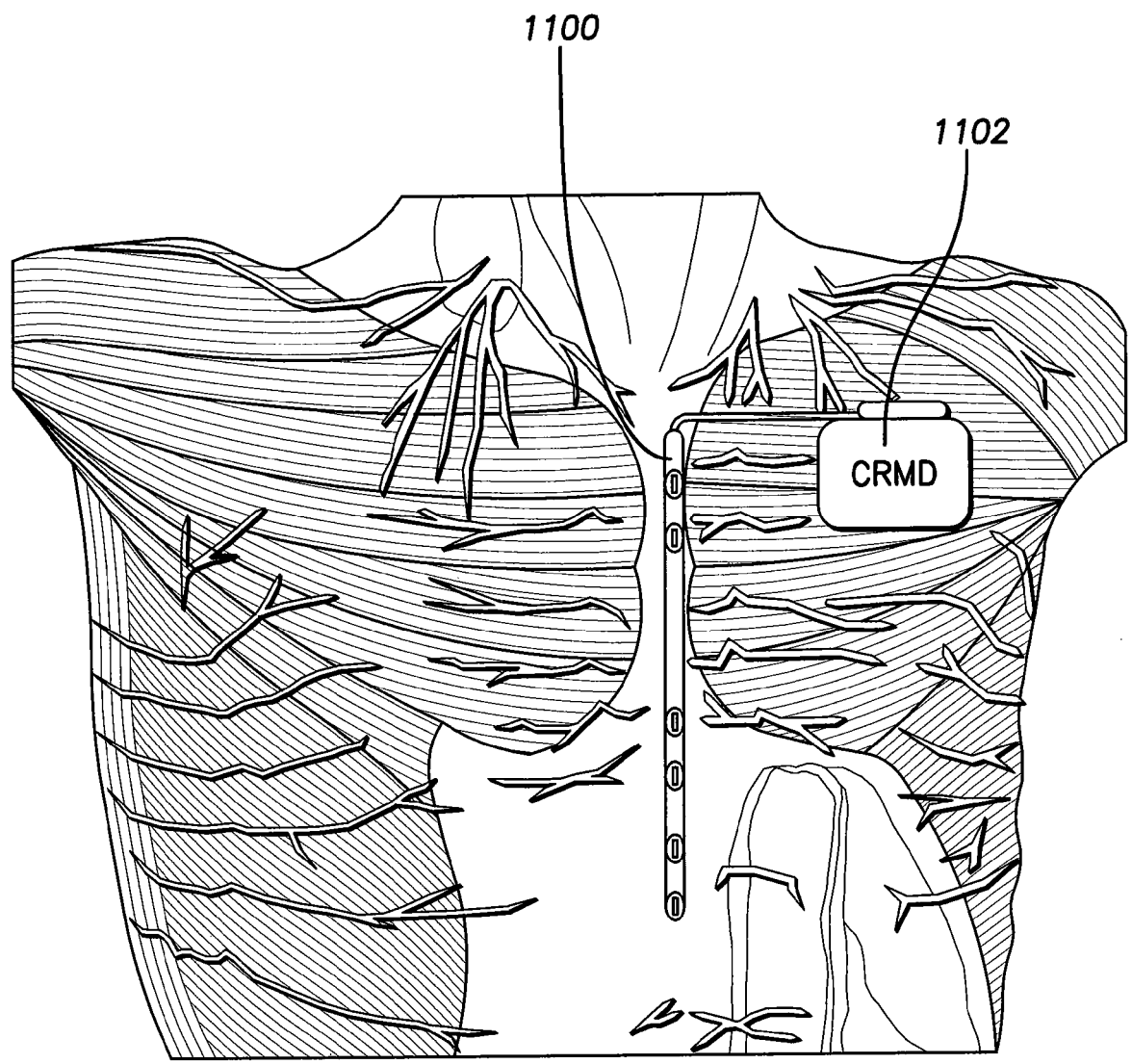
FIG. 13 illustrates the exemplary CRMD of FIG. 1, along with a set of percutaneous neurostimulation leads implanted along the sternum of a patient with three pair of bipolar electrodes.

FIG. 13 illustrates a lead arrangement for percutaneous implant wherein a lead 1100 is implanted along the sternum (STN) having a set of linear electrodes (similar to those used for SCS) for use with a CRMD 1102. In this example, the lead has three pairs of bipolar electrodes for use in stimulating the H1, H2+ and H2− sites. Although not shown in this particular figure, the CRMD will also include one or more cardiac pacing/sensing leads.

Figure 14:
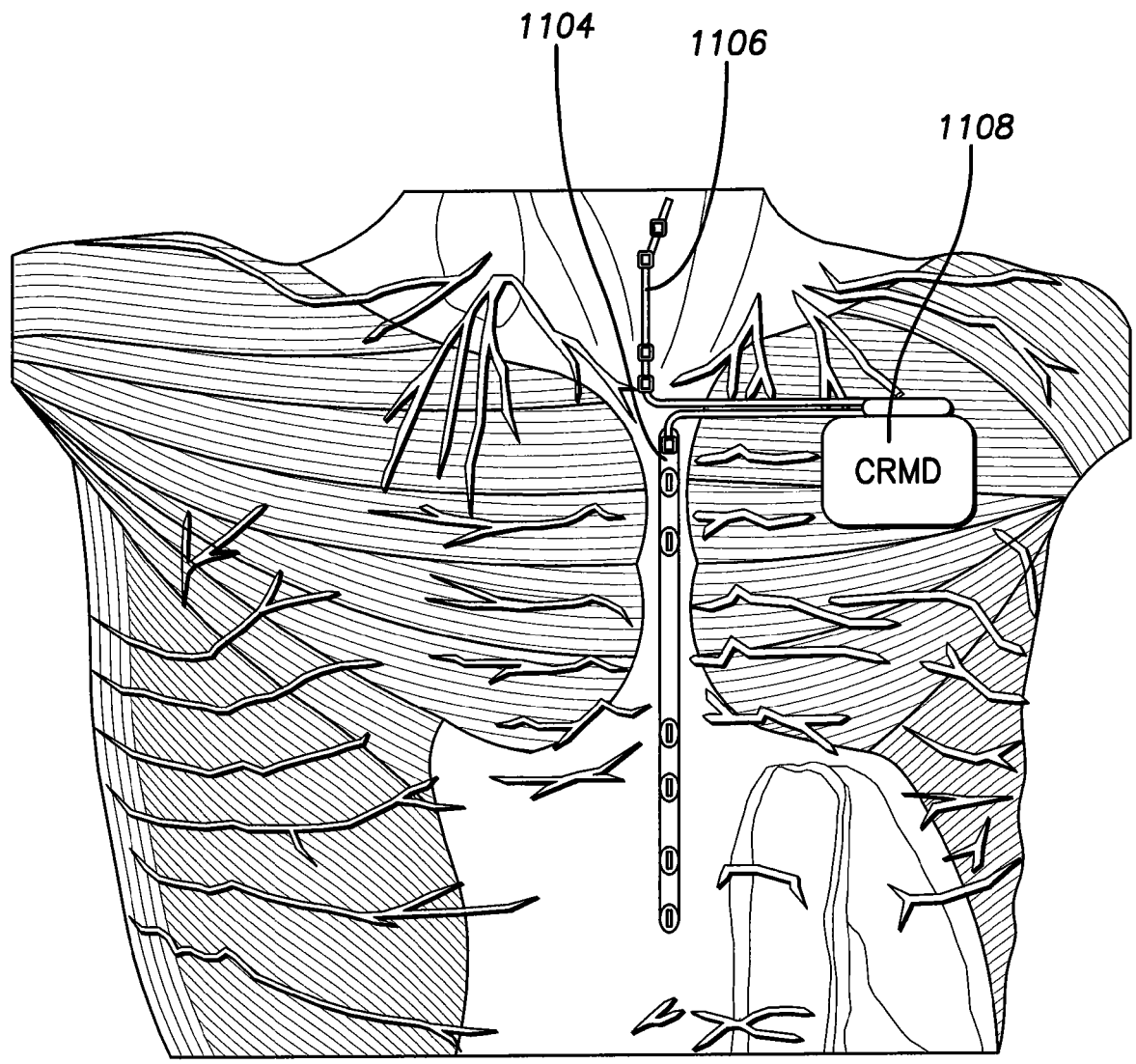
FIG. 14 illustrates the exemplary configuration of FIG. 13, along with an additional set of subcutaneous neurostimulation leads implanted in the neck with two pair of bipolar electrodes.

FIG. 14 illustrates a lead arrangement for subcutaneous implant wherein a lead 1104 is implanted along the sternum and another lead 1106 is implanted along the neck, each separately connected to the CRMD 1108. Alternatively, lead 1104 can be implanted under the sternum. In either case, the stimulation configuration can be all cathodes on the STN lead and all anodes on the other lead. Again, although not shown, the CRMD will also include one or more cardiac pacing/sensing leads.

Figure 15:
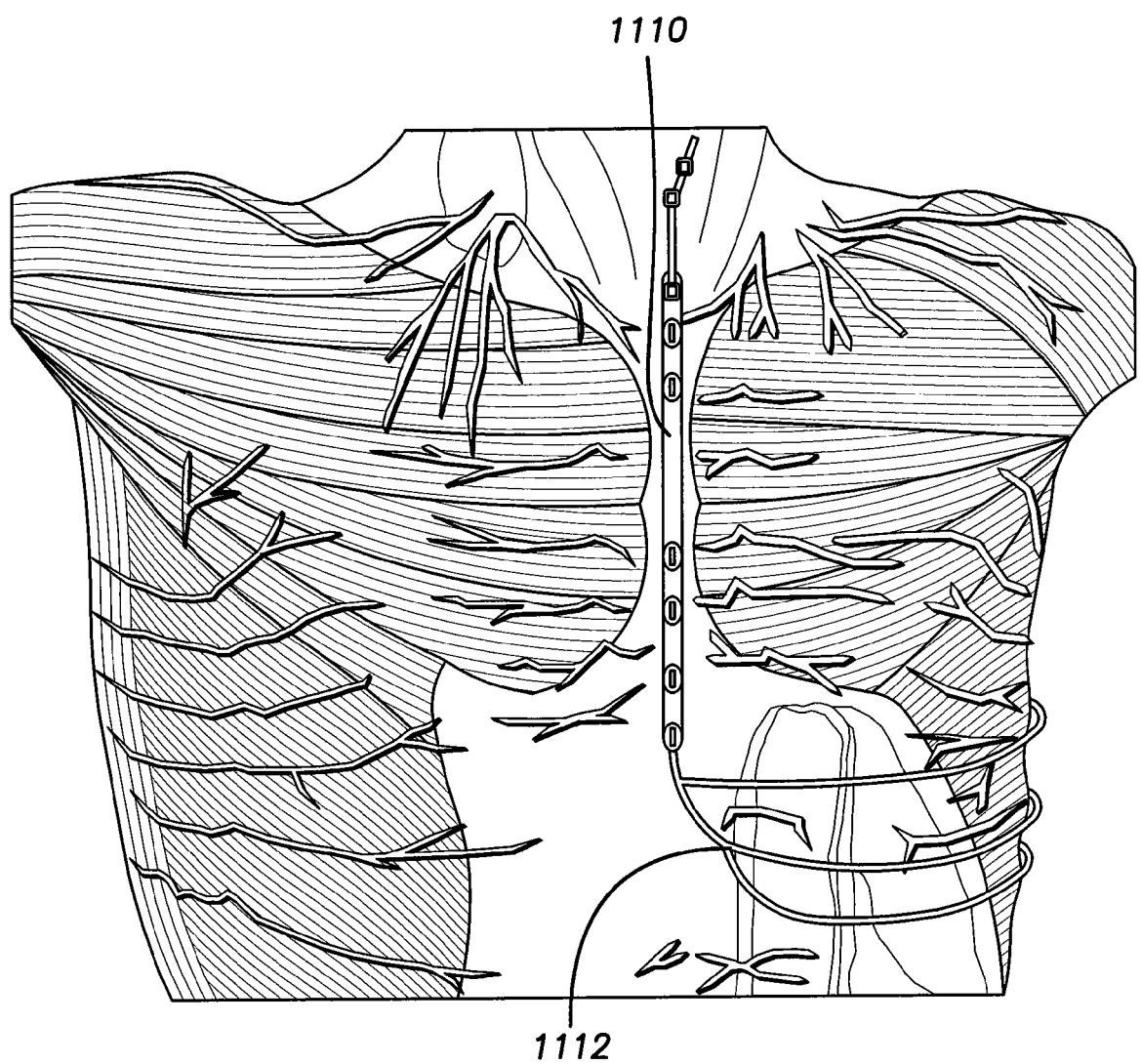
FIG. 15 illustrates an alternative configuration of neurostimulation leads that may be used with the CRMD of FIG. 1, wherein the lead includes three pair of electrodes along the sternum as well as a subcutaneous finger array within the abdomen.

FIG. 15 illustrates a lead arrangement having a linear lead 1110 implanted along the sternum for neurostimulation, where the lead also includes a subcutaneous finger array portion 1112 for delivering defibrillation shocks to sites in the abdomen (wherein a finger array is a type of pericardial pacing and sensing system including thin "finger-like" electrodes or leads that may be linear or flexible and may include coils.) In this example, neither the CRMD (ICD) nor the cardiac/pacing leads are shown. The STN leads can be connected or integrated with a CRMD device implanted in abdominal regions such as an ICD implanted in the abdomen. For example, the CRMD can be integrated with a subcutaneous finger array of an ICD/CRT-D.

Figure 16:
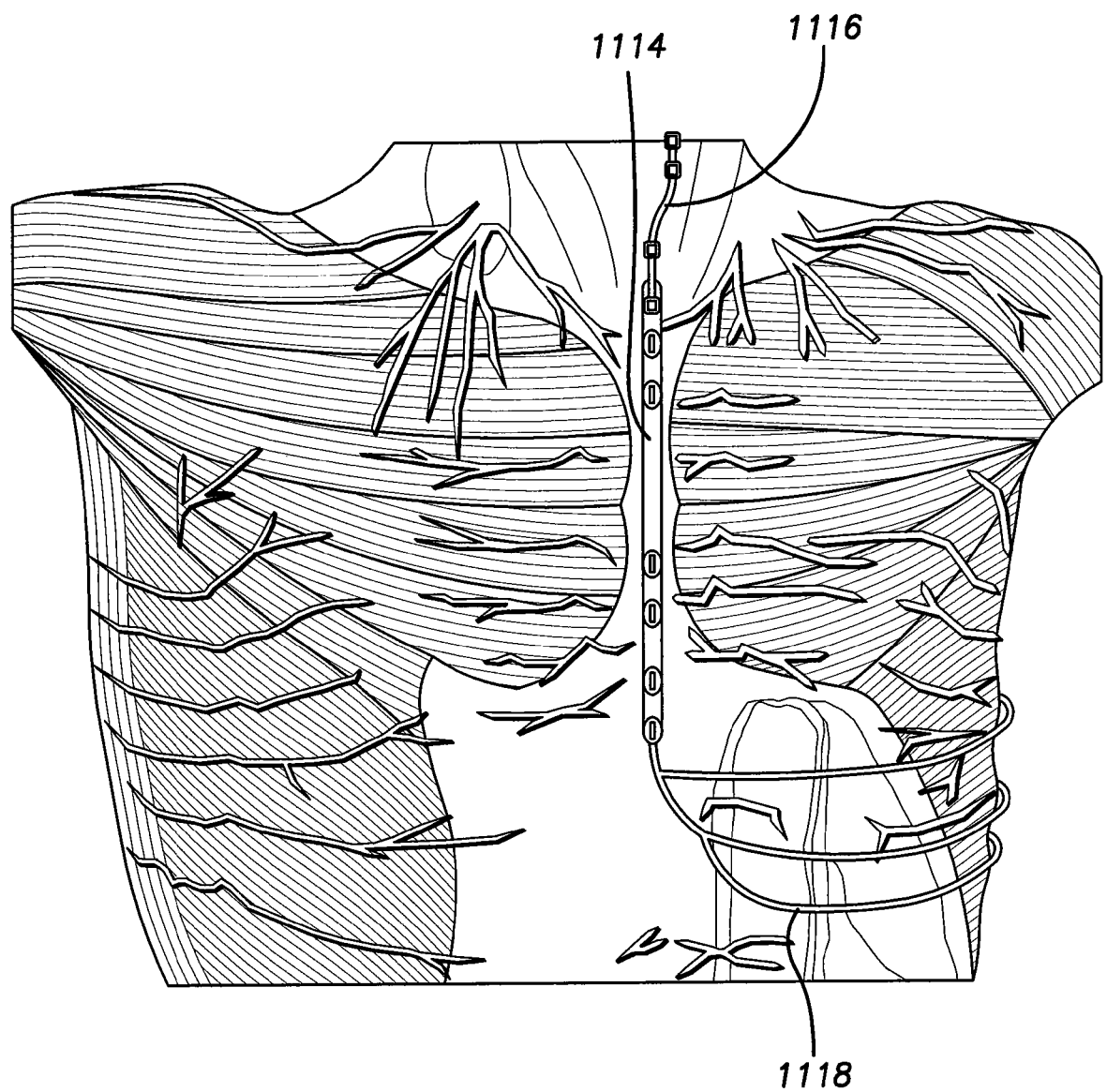
FIG. 16 illustrates a configuration of neurostimulation leads similar to that of FIG. 15 but additionally including two pair of electrodes along the neck.

FIG. 16 illustrates a lead arrangement having a linear lead 1114 implanted along the sternum for neurostimulation with a subcutaneous portion 1116 along the neck, also for neurostimulation, where the lead also includes a subcutaneous finger array portion 1118 for delivering defibrillation shocks to sites in the abdomen. In this example, neither the CRMD (ICD) nor the cardiac/pacing leads are shown.

Figure 17:
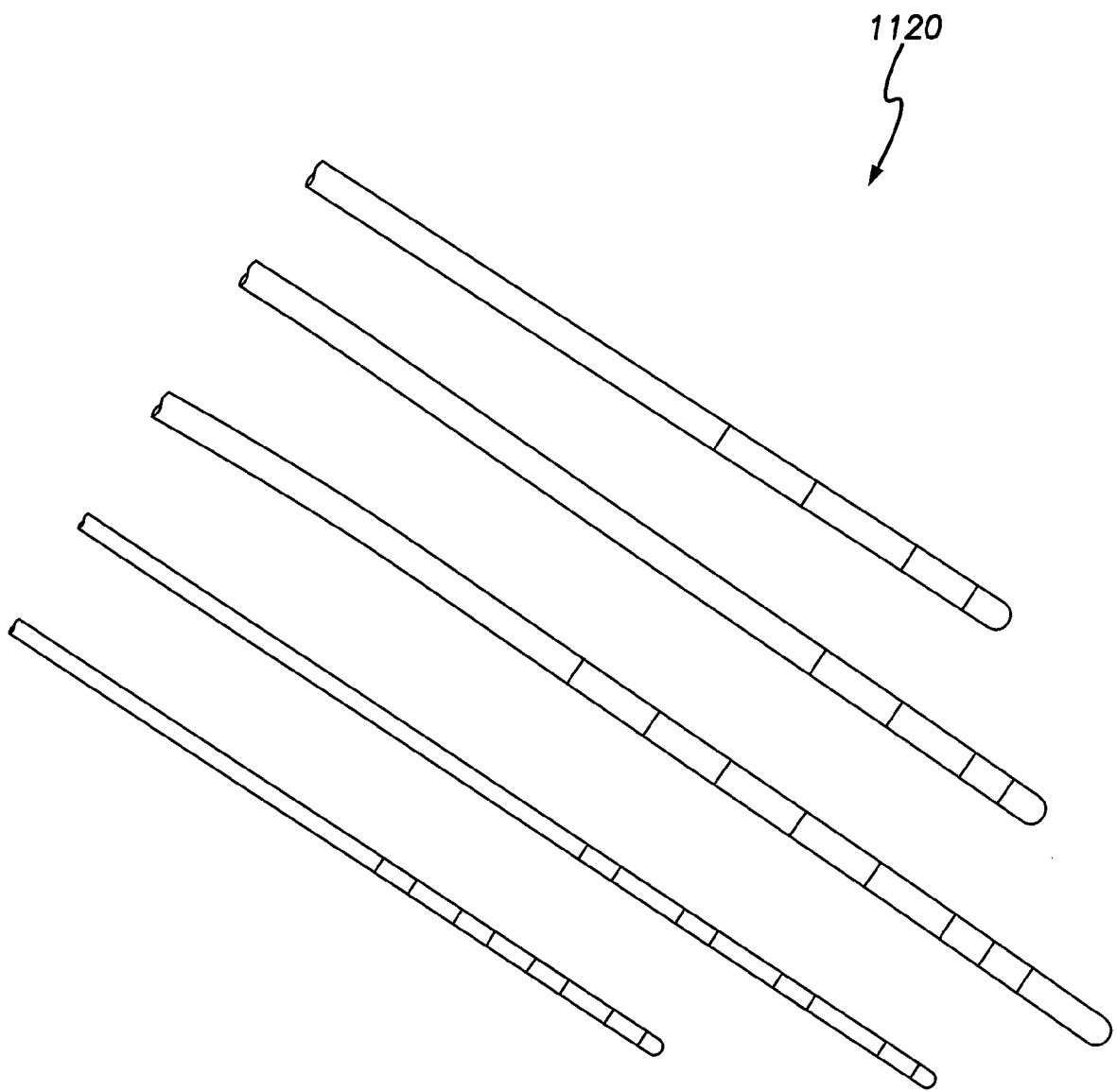
FIG. 17 illustrates percutaneous leads that may be used with the CRMD of FIG. 1 in various embodiments.
Figure 18:
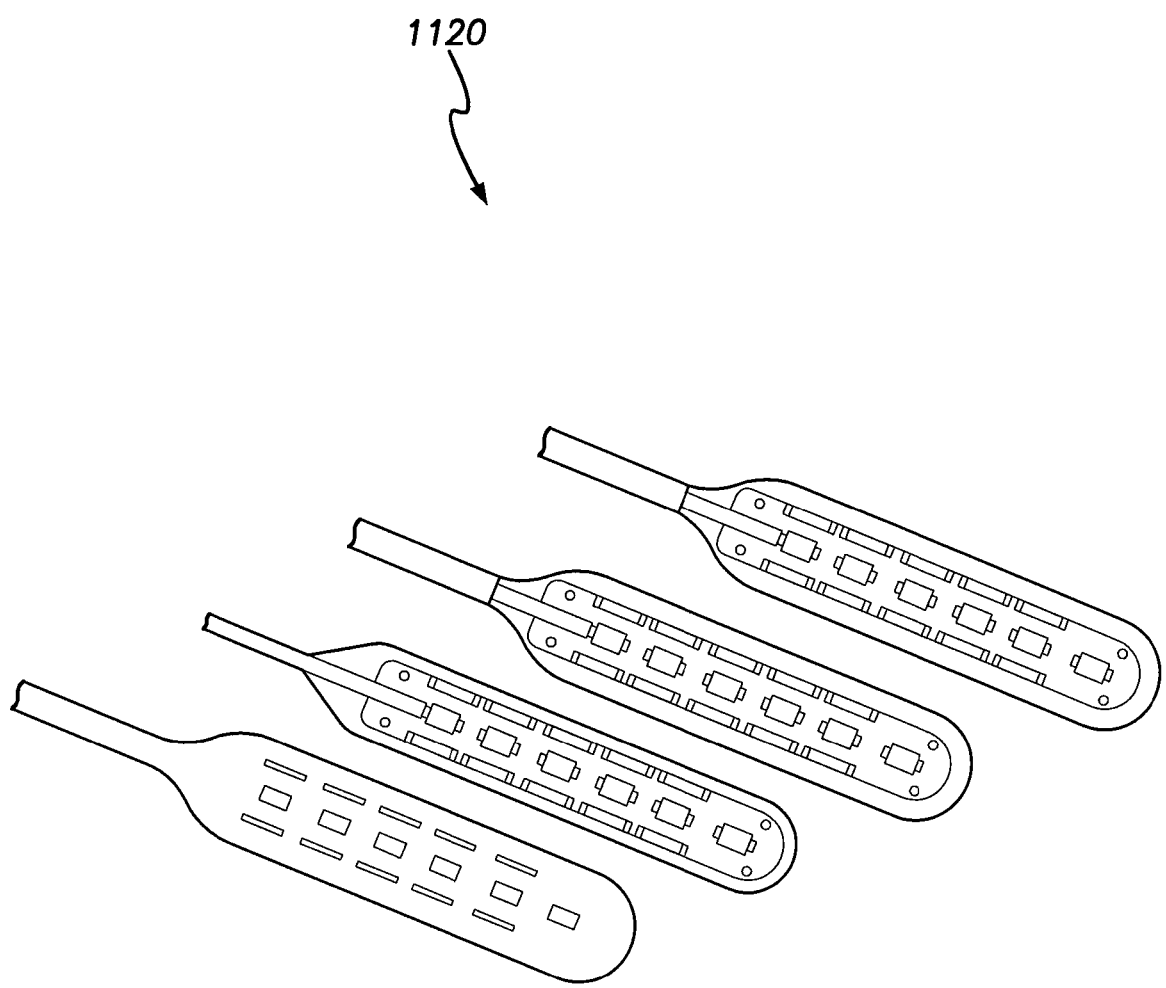
FIG. 18 illustrates surgical patches that may be used with the CRMD of FIG. 1 in various embodiments.
Figure 19:
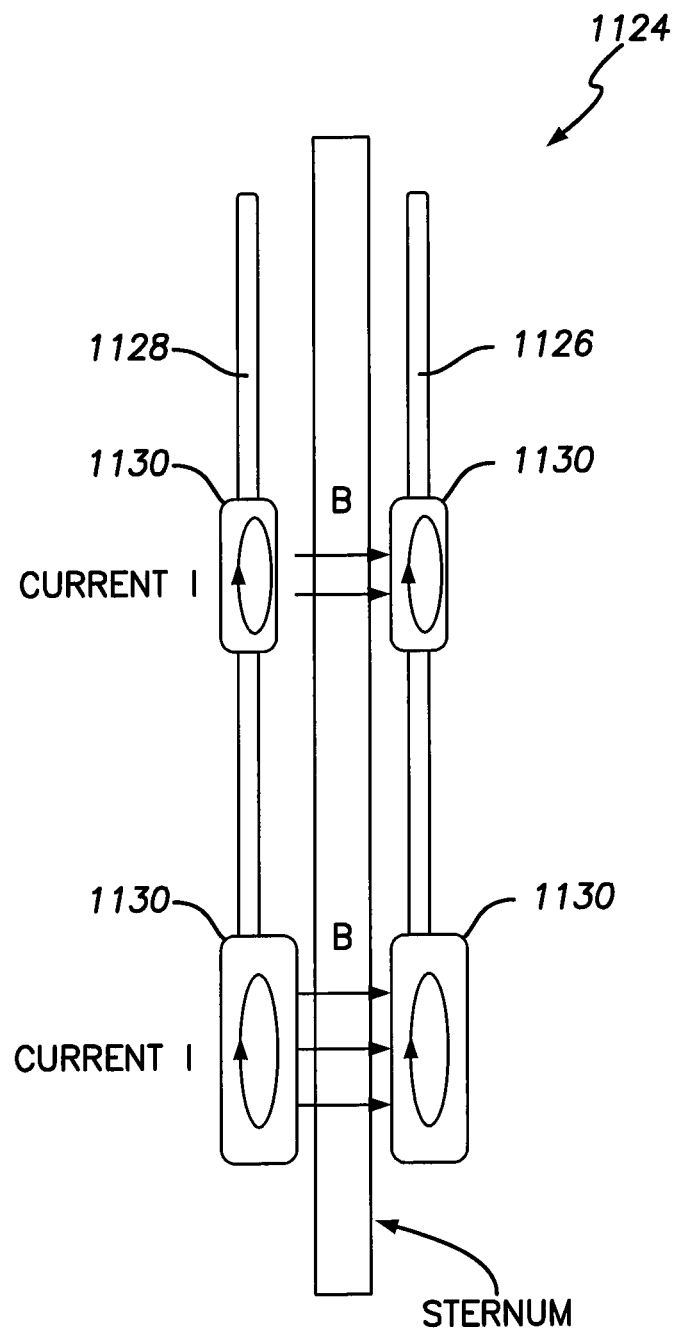
FIG. 19 illustrates particular configurations exploiting the surgical patches of FIG. 18 where magnetic fields cab be induced for neurostimulation.

FIG. 17 illustrates a set of percutaneous leads 1120 (shown outside the body) of differing sizes, which may be used in at least some of the embodiments of FIGS. 13-16. FIG. 18 illustrates a set of surgical patch leads 1122 of differing sizes and configurations (shown outside the body), which may be used in at least some of the embodiments of FIGS. 13-16. These patches may be the same or similar to patches used for SCS. FIG. 19 illustrates a pair of leads 1124, which may be used in at least some of the embodiments, wherein two leads (one subcutaneous, e.g., 1126 and the other sub-sternum, e.g. 1128) are provided with stimulation patches 1130 configured to create a magnetic field B through selected stimulation sites that is induced by electrical current from the leads, as shown.

What have been described thus far are systems and techniques primarily directed to stimulating sites within anterior regions of the neck, thorax and abdomen, particularly neurostimulation sites at or near each of the H1, H2+, H2−, L1, L2, P1 and P2 acupuncture sites. Possible advantages of these stimulation techniques over SCS techniques include use of a single device for both CRMD and neurostimulation innovations that allow feature interactions such as: HF monitoring (impedance, ER, conduction delays etc) with effect of neurostimulation; managing PA pressure or LAP or estimated PA pressures from RV dP/dt max by stimulating nerves; prevention of arrhythmia by using PAC or PVC counts, HRV or HRT to trigger neurostimulation; synchronization of AF suppression or ATP and neurostimulation; synchronization of shock (AF or VT/VF) and neurostimulation pulse trains; detecting sleep apnea (using impedance etc) and delivering neurostimulation therapies; and detection of ischemia and delivering neurostimulation therapies In some examples, these techniques may be exploited in conjunction with techniques that stimulate others sites (including SCS sites), such as posterior sites along the spine. In the regard, internal research (not yet published) has investigated the applications of SCS in CRMD and its new indications with objectives on: whether upper thoracic (T1-T5) SCS protects against induction and/or maintenance of AF; whether upper thoracic (T1-T5) SCS can mitigate adverse remodeling and tachyarrhythmias associated with worsening heart failure; and to investigate the effects of upper thoracic (T1-T5) and lower thoracic/lumbar (T11-L2) SCS on blood pressure and flow using various stimulation parameters. An on-going animal study in fifteen surviving canines (n=7 untreated AF control, n=5 with SCS therapy applied early in paroxysmal AF development, n=3 with SCS therapy applied late after chronic AF developed) showed three out of five responders to SCS in T1-T5 among the early SCS group, as measured by AF Burden (fraction of time in auto mode switch of the total time not tachypacing to induce AF). Further investigation of the baseline characteristics of individuals, SCS thresholds, and possibly other parameters may elucidate differences between responders and non-responders in this study.

In another study, chronic HF canine models were created by MI and MR in n=8 untreated HF control, n=8 early SCS (with regard to HF development), and n=8 late SCS (with regard to HF development). The study is on-going and current data in n=3 control and n=4 early SCS showed SCS can have profound effect in preventing dilation of LVEDV and LA volume in two out four early SCS group. The same two treated subjects show positive response in various measures of heart rate variability, indicating that in these subjects the balance between sympathetic and parasympathetic activation is maintained to levels that are more normal. To increase the responder rate to SCS, the underlined mechanism needs to be further explored for optimizing device implementation. In yet another study, in n=7 swine with Normotensive and Ang-II HTN porcine models, SCS in T11-L1 showed modest reduction in arterial blood pressure simultaneously with improved LV dP/dtmax. Combining SCS T11-L1 with T1-T5 tended to enhance the effects.

These preliminary results suggest that neurostimulation at the posterior thoracic sites may be useful as well, in conjunction with the anterior-based techniques described above. It is also note that Chinese traditional medicine and Acupuncture were developed hundreds years based on clinical practice that did not come along with theoretical basis of Western medicine but connections between Chinese medicine/Acupuncture are being recognized today. For example, the site below T5 is called "God channel" and is deemed to be special to protecting heart so that it is also called "heart protecting God." It was described in Chinese medicine that this site has a very important role for blood circulation to the heart, preventing or treating ischemia. This is indicates that stimulating T1-T5 may impact cardio-vascular and cardiac functions. Acupuncture indicates that T5 could be the critical site among T1-T5. Accordingly, stimulation at T5 or other SCS sites may be beneficial in conjunction with stimulation at H1, H2+, H2−, L1, L2, P1 and P2.

See, also, techniques described in U.S. patent application Ser. No. 13/485,404 of Bharmi et al., filed May 31, 2012, entitled "Systems and Methods for Controlling Neurostimulation based on Regional Cardiac Performance for use by Implantable Medical Devices" and U.S. patent application Ser. No. 13/442,749 of Xi et al., filed Apr. 9, 2012, entitled "Systems and Methods for Controlling Spinal Cord Stimulation to Improve Stimulation Efficacy for Use By Implantable Medical Devices."

The above-described systems and techniques can be implemented with a variety of implantable medical devices. For the sake of completeness, a CRMD implementation will now be described in detail.

Exemplary CRMD

Figure 21:
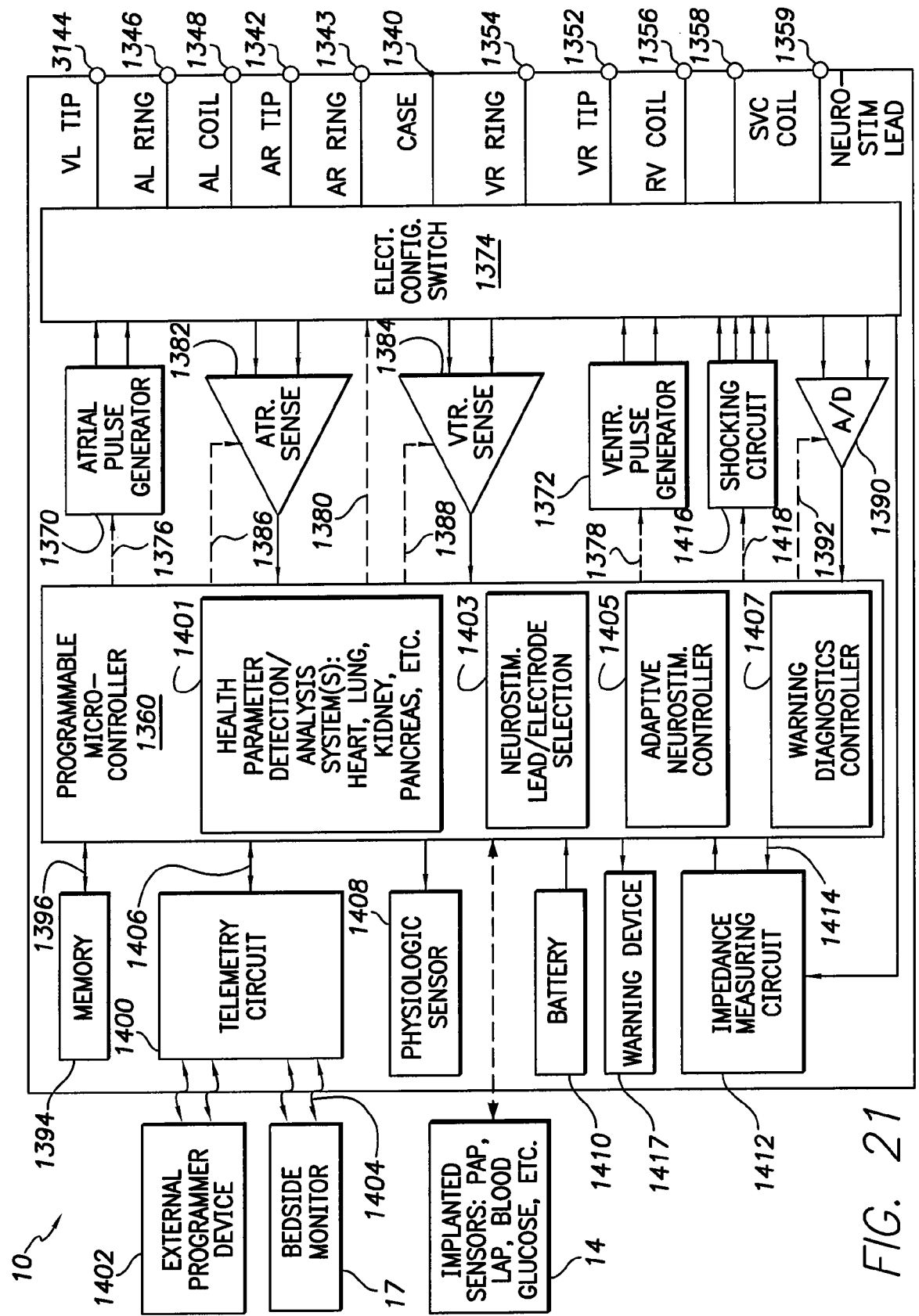
FIG. 21 is a functional block diagram of the CRMD of FIG. 20, illustrating basic device circuit elements that provide cardioversion, defibrillation and/or pacing stimulation in four chambers of the heart, and particularly illustrating components within the device for controlling neurostimulation.

With reference to FIGS. 20 and 21, a description of an exemplary CRMD will now be provided, which is equipped to control neurostimulation, as well as to control a wide variety of other functions. FIG. 20 provides a simplified block diagram of the CRMD, which is a dual-chamber stimulation device capable of treating both fast and slow arrhythmias with stimulation therapy, including cardioversion, defibrillation, and pacing stimulation. To provide atrial chamber pacing stimulation and sensing, CRMD 10 is shown in electrical communication with a heart 1312 by way of a right atrial lead 1320 having an atrial tip electrode 1322 and an atrial ring electrode 1323 implanted in the atrial appendage. RA lead 1320 also has a physiological sensor 14 for transseptal implant into the LA. See, for example, U.S. patent application Ser. No. 11/856,443, filed Sep. 17, 2007 of Zhao et al., entitled "MEMS-Based Left Atrial Pressure Sensor for use with an Implantable Medical Device" (now abandoned), which is assigned to the assignee of rights to the present application. This is just one example of a physiological sensor that may be used to detect parameters used to control neurostimulation. As explained, the location and type of sensor will depend on the particular parameter(s) to be detected. In some cases, the sensor will be a component of the CRMD itself. This is particularly common for sensors configured to sense parameters based on an analysis of impedance signals.

CRMD 10 is also in electrical communication with the heart by way of a right ventricular lead 1330 having, in this embodiment, a ventricular tip electrode 1332, a right ventricular ring electrode 1334, a right ventricular (RV) coil electrode 1336, and a superior vena cava (SVC) coil electrode 1338. Typically, the right ventricular lead 1330 is transvenously inserted into the heart so as to place the RV coil electrode 1336 in the right ventricular apex, and the SVC coil electrode 1338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, CRMD 10 is coupled to a CS lead 1324 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 1324 is designed to receive atrial and ventricular cardiac signals and to deliver left ventricular pacing therapy using at least a left ventricular tip electrode 1326, left atrial pacing therapy using at least a left atrial ring electrode 1327, and shocking therapy using at least a left atrial coil electrode 1328. With this configuration, biventricular pacing can be performed. Although only three leads are shown in FIG. 20, it should also be understood that additional stimulation leads (with one or more pacing, sensing and/or shocking electrodes) might be used in order to efficiently and effectively provide pacing stimulation to the left side of the heart or atrial cardioversion and/or defibrillation. Also, leads with more or fewer electrodes may be used, such as the Quartet™ lead of St. Jude Medical.

Additionally, as shown, a lead 1329 is provided for connecting the CRMD to one or more neurostimulation electrodes or patches such as device 16 of FIG. 1. Additional neurostimulation leads may be required depending upon the number of neurostimulation sites and the configuration of individual leads.

A simplified block diagram of internal components of CRMD 10 is shown in FIG. 21. While a particular CRMD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned stroke/cardiac ischemia detection and discrimination.

The housing or case of 1340 for CRMD 10, shown schematically in FIG. 21, is often referred to as the "can", "case" or "case electrode" and may be programmably selected to act as the return electrode for all "unipolar" modes. The housing 1340 may further be used as a return electrode alone or in combination with one or more of the coil electrodes, 1328, 1336 and 1338, for shocking purposes. The housing 1340 further includes a connector (not shown) having a plurality of terminals, 1342, 1343, 1344, 1346, 1348, 1352, 1354, 1356, 1358 and 1359 (shown schematically and, for convenience, the names of the electrodes to which they are connected are shown next to the terminals). As such, to achieve right atrial sensing and pacing, the connector includes at least a right atrial tip terminal ($A_R$ TIP) 1342 adapted for connection to the atrial tip electrode 1322 and a right atrial ring ($A_R$ RING) electrode 1343 adapted for connection to right atrial ring electrode 1323. To achieve left chamber sensing, pacing and shocking, the connector includes at least a left ventricular tip terminal ($V_L$ TIP) 1344, a left atrial ring terminal ($A_L$ RING) 1346, and a left atrial shocking terminal ($A_L$ COIL) 1348, which are adapted for connection to the left ventricular ring electrode 1326, the left atrial ring electrode 1327, and the left atrial coil electrode 1328, respectively. To support right chamber sensing, pacing and shocking, the connector further includes a right ventricular tip terminal ($V_R$ TIP) 1352, a right ventricular ring terminal ($V_R$ RING) 1354, a right ventricular shocking terminal ($V_R$ COIL) 1356, and an SVC shocking terminal (SVC COIL) 1358, which are adapted for connection to the right ventricular tip electrode 1332, right ventricular ring electrode 1334, the $V_R$ coil electrode 1336, and the SVC coil electrode 1338, respectively. A terminal 1359 is shown for connection to the neurostimulation lead system. Depending upon the particular lead system, additional terminals may be needed.

Implanted physiological sensor 14 is shown in FIG. 21 (which may include including or incorporate PAP sensors, LAP sensors, blood glucose sensors or other sensors.) As can be appreciated, more or fewer sensors can be provided. The sensors can be physically separate from one another. Also, additional terminals may be provided for use with the various sensors (which, for simplicity, are shown functionally connected to the CRMD via a dashed line.) An integrated sensor providing a variety of sensor functions is described in pending U.S. patent application Ser. No. 11/927,026, filed Oct. 29, 2007 of Nabutovsky et al. As already noted, the sensor may exploit MEMS technology as described in the patent application to Zhao, cited above.

At the core of CRMD 10 is a programmable microcontroller 1360, which controls the various modes of stimulation therapy. As is well known in the art, the microcontroller 1360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 1360 includes the ability to process or monitor input signals (data) as controlled by a program code stored in a designated block of memory. The details of the design and operation of the microcontroller 1360 are not critical to the invention. Rather, any suitable microcontroller 1360 may be used that carries out the functions described herein. The use of microprocessor-based control circuits for performing timing and data analysis functions are well known in the art.

As shown in FIG. 21, an atrial pulse generator 1370 and a ventricular pulse generator 1372 generate pacing stimulation pulses for delivery by the right atrial lead 1320, the right ventricular lead 1330, and/or the CS lead 1324 via an electrode configuration switch 1374. It is understood that in order to provide stimulation therapy in each of the four chambers of the heart, the atrial and ventricular pulse generators, 1370 and 1372, may include dedicated, independent pulse generators, multiplexed pulse generators or shared pulse generators. The pulse generators, 1370 and 1372, are controlled by the microcontroller 1360 via appropriate control signals, 1376 and 1378, respectively, to trigger or inhibit the stimulation pulses.

The microcontroller 1360 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 1374 includes a plurality of switches for connecting the desired electrodes to the appropriate I/O circuits, thereby providing complete electrode programmability. Accordingly, the switch 1374, in response to a control signal 1380 from the microcontroller 1360, determines the polarity of the stimulation pulses (e.g., unipolar, bipolar, combipolar, etc.) by selectively closing the appropriate combination of switches (not shown) as is known in the art.

Atrial sensing circuits 1382 and ventricular sensing circuits 1384 may also be selectively coupled to the right atrial lead 1320, CS lead 1324, and the right ventricular lead 1330, through the switch 1374 for detecting the presence of cardiac activity in each of the four chambers of the heart. Accordingly, the atrial (ATR. SENSE) and ventricular (VTR. SENSE) sensing circuits, 1382 and 1384, may include dedicated sense amplifiers, multiplexed amplifiers or shared amplifiers. The switch 1374 determines the "sensing polarity" of the cardiac signal by selectively closing the appropriate switches, as is also known in the art. In this way, the clinician may program the sensing polarity independent of the stimulation polarity. Each sensing circuit, 1382 and 1384, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The automatic gain/sensitivity control enables CRMD 10 to deal effectively with the difficult problem of sensing the low amplitude signal characteristics of atrial or ventricular fibrillation. The outputs of the atrial and ventricular sensing circuits, 1382 and 1384, are connected to the microcontroller 1360 which, in turn, are able to trigger or inhibit the atrial and ventricular pulse generators, 1370 and 1372, respectively, in a demand fashion in response to the absence or presence of cardiac activity in the appropriate chambers of the heart.

For arrhythmia detection, CRMD 10 utilizes the atrial and ventricular sensing circuits, 1382 and 1384, to sense cardiac signals to determine whether a rhythm is physiologic or pathologic. As used in this section, "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 1360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (ND) data acquisition system 1390. The data acquisition system 1390 is configured to acquire intracardiac electrogram signals, convert the raw analog data into a digital signal, and store the digital signals for later processing and/or telemetric transmission to an external device 1402. The data acquisition system 1390 is coupled to the right atrial lead 1320, the CS lead 1324, and the right ventricular lead 1330 through the switch 1374 to sample cardiac signals across any pair of desired electrodes. The microcontroller 1360 is further coupled to a memory 1394 by a suitable data/address bus 1396, wherein the programmable operating parameters used by the microcontroller 1360 are stored and modified, as required, in order to customize the operation of CRMD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable CRMD 10 may be non-invasively programmed into the memory 1394 through a telemetry circuit 1424 in telemetric communication with the external device 1402, such as a programmer, transtelephonic transceiver or a diagnostic system analyzer. The telemetry circuit 1424 is activated by the microcontroller by a control signal 1406. The telemetry circuit 1424 advantageously allows intracardiac electrograms and status information relating to the operation of CRMD 10 (as contained in the microcontroller 1360 or memory 1394) to be sent to the external device 1402 through an established communication link 1404. The telemetry circuit also receives/transmits signals to bedside monitor 17, including the aforementioned diagnostic data.

CRMD 10 further includes an accelerometer or other physiologic sensor 1408, commonly referred to as a "rate-responsive" sensor because it is typically used to adjust pacing stimulation rate according to the exercise state of the patient. However, the physiological sensor 1408 may further be used to detect changes in cardiac output, changes in the physiological condition of the heart, or diurnal changes in activity (e.g., detecting sleep and wake states) and to detect arousal from sleep. Accordingly, the microcontroller 1360 responds by adjusting the various pacing parameters (such as rate, AV delay, V-V delay, etc.) at which the atrial and ventricular pulse generators, 1370 and 1372, generate stimulation pulses. While shown as being included within CRMD 10, it is to be understood that the physiologic sensor 1408 may also be external to CRMD 10, yet still be implanted within or carried by the patient. A common type of rate responsive sensor is an activity sensor incorporating an accelerometer or a piezoelectric crystal, which is mounted within the housing 1340 of CRMD 10. Other types of physiologic sensors are also known, for example, sensors that sense the oxygen content of blood, respiration rate and/or minute ventilation, pH of blood, ventricular gradient, etc.

The CRMD additionally includes a battery 1426, which provides operating power to all of the circuits shown in FIG. 21. The battery 1426 may vary depending on the capabilities of CRMD 10. For CRMD 10, which employs shocking therapy, the battery 1426 should be capable of operating at low current drains for long periods, and then be capable of providing high-current pulses (for capacitor charging) when the patient requires a shock pulse. The battery 1426 must also have a predictable discharge characteristic so that elective replacement time can be detected. Accordingly, CRMD 10 is preferably capable of high voltage therapy and appropriate batteries.

As further shown in FIG. 21, CRMD 10 is shown as having an impedance measuring circuit 1412, which is enabled by the microcontroller 1360 via a control signal 1414. Uses for an impedance measuring circuit include, but are not limited to, detecting cardiogenic and transthoracic impedance as discussed above, as well as, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; and detecting the opening of heart valves, etc. The impedance measuring circuit 120 is advantageously coupled to the switch 144 so that any desired electrode may be used.

In the case where CRMD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 1360 further controls a shocking circuit 1416 by way of a control signal 1418. The shocking circuit 1416 generates shocking pulses of low (up to 0.5 joules), moderate (0.5-10 joules) or high energy (11 to 40 or more joules), as controlled by the microcontroller 1360. Such shocking pulses are applied to the heart of the patient through at least two shocking electrodes, and as shown in this embodiment, selected from the left atrial coil electrode 1328, the RV coil electrode 1336, and/or the SVC coil electrode 1338. The housing 1340 may act as an active electrode in combination with the RV electrode 1336, or as part of a split electrical vector using the SVC coil electrode 1338 or the left atrial coil electrode 1328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 14-40 or more joules), delivered asynchronously (since R-waves may be too disorganized), and pertaining exclusively to the treatment of fibrillation. Accordingly, the microcontroller 1360 is capable of controlling the synchronous or asynchronous delivery of the shocking pulses.

Insofar as neurostimulation is concerned, the microcontroller includes a health parameter detection/analysis system 1401 operative to detect and analyze parameters associated with the health of the patient such parameters representative of the health of the heart, lungs, kidneys, etc., detected by the various sensors or detected within IEGM signals or impedance signals, as explained above with reference to FIGS. 2-11. The microcontroller also includes a neurostimulation lead/electrode selection system 1403 operative to select particular electrodes within particular neurostimulation leads for delivery of neurostimulation to selected acupuncture sites, as also explained above. An adaptive neurostimulation controller 1405 operates to automatically adjust the neurostimulation based on changes, if any, in the parameters detected by system 1401 in an attempt to address any adverse health conditions (as explained above.) A warning/diagnostics controller 1407 controls the generation of warning signals (via, e.g., a warning device 1417) as to any adverse health conditions and controls the recording of diagnostics (using memory 1394) pertaining to those conditions or any treatment delivered in response thereto.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using ASICs or the like.

The principles of the invention may be exploiting using other implantable systems or in accordance with other techniques. Thus, while the invention has been described with reference to particular exemplary embodiments, modifications can be made thereto without departing from scope of the invention. Note also that the term "including" as used herein is intended to be inclusive, i.e. "including but not limited to."

What is claimed is:

1. A method for use with an implantable medical system for implant within a patient where the implantable medical system is equipped for neurostimulation, the system comprising:
    detecting, with the implantable medical system, a parameter representative of one of more of: heart failure; arrhythmia; atrial tachycardia/atrial fibrillation (AT/AF) burden; hypertension; Cheyne-Stokes respiration (CSR) sleep apnea; cardiac ischemia; and angina; and
    in response to the detected parameter, delivering neurostimulation, via the implantable medical system, to one or more acupuncture sites within anterior regions of one or more of the neck, thorax and abdomen of the patient;
    wherein if the detected parameter includes parameters representative of hypertension, the acupuncture sites for delivery of the neurostimulation includes one or more of acupuncture sites P1 and P2;
    and further wherein if the detected parameter includes parameters representative of at least one of CSR and sleep apnea, the acupunctures sites for delivery of the neurostimulation includes one or more of acupuncture sites L1 and L2.

2. The method of claim 1 wherein neurostimulation is delivered to acupuncture sites that include one of more of: H1, H2+, H2−, L1, L2, P1 and P2.

3. The method of claim 1 wherein the detected parameters are representative of heart failure and wherein the acupuncture sites for delivery of the neurostimulation include one or more of H1, H2+ and H2− sites.

4. The method of claim 3 wherein the parameters representative of heart failure include one or more of: impedance parameters; evoked response (ER) parameters; intracardiac electrogram (IEGM) conduction delay parameters; cardiogenic impedance (Zc) conduction delay parameters; left atrial (LA) pressure; pulmonary artery (PA) pressure; or right ventricular (RV) pressure.

5. The method of claim 3 wherein the neurostimulation is delivered to achieve one or more of: reverse modeling of the heart and mitigation of heart failure progression.

6. The method of claim 1 wherein the detected parameters are representative of arrhythmia and wherein the acupuncture sites for delivery of the neurostimulation include one or more of H1, H2+ and H2− sites.

7. The method of claim 6 wherein the parameters representative of arrhythmia include one or more of: AT parameters, AF parameters, ventricular fibrillation (VF) parameters, an AT/AF burden; a premature atrial contraction (PAC) count; a premature ventricular contraction (PVC) count; a heart rate variability (HRV) value; a heart rate turbulence (HRT) value; a dispersion of conduction delays value; and an antitachycardia pacing (ATP) success rate.

8. The method of claim 7 wherein the neurostimulation is delivered to achieve or more of: prevention of an arrhythmia; reduction of AT/AF burden; and an improvement in ATP success rate.

9. The method of claim 1 wherein the parameters representative of hypertension include one or more of: pulmonary artery pressure (PAP) values; left atrial pressure (LAP) values; and estimated PAP pressure derived from a maximum rate of change in right ventricular (RV) pressure (RV dP/dt max.)

10. The method of claim 1 wherein the neurostimulation is delivered to reduce hypertension.

11. The method of claim 1 wherein the parameters representative of at least one of CSR and sleep apnea include respiratory signals derived from impedance signals.

12. The method of claim 1 wherein the neurostimulation is delivered to achieve one or more of: a reduction in CSR and a reduction in sleep apnea.

13. The method of claim 1 wherein the detected parameters are representative of one or more of cardiac ischemia and angina and wherein the acupuncture sites for delivery of the neurostimulation include one or more of the H1, H2+ and H2− sites.

14. The method of claim 13 wherein the parameters representative of one or more of ischemia and angina include IEGM parameters.

15. The method of claim 13 wherein the neurostimulation is delivered to achieve one or more of: a reduction in cardiac ischemia and a reduction in angina.

16. The method of claim 1 further including controlling the neurostimulation therapy in conjunction with delivery of therapeutic shocks.

17. The method of claim 16 wherein neurostimulation is controlled in to reduce shock pain using neurostimulation delivered at one or more of the H1, H2+ and H2− acupuncture sites.

18. The method of claim 1 wherein the steps are performed by an implantable cardiac rhythm management device (CRMD) in conjunction within one or more implantable neurostimulation leads.

19. The method of claim 1 wherein the neurostimulation is delivered using one or more of: a simultaneous stimulation pattern; a sequential stimulation pattern; or a combination of simultaneous and sequential stimulation patterns.

20. The method of claim 1 wherein the neurostimulation is delivered using one or more of: electrical stimulation; thermal stimulation; and magnetic stimulation.

21. An implantable medical system for implant within a patient, the system comprising:
    a neurostimulation lead system configured to deliver neurostimulation to one or more acupuncture sites within an anterior region of one or more of the neck, thorax and abdomen of the patient, the neurostimulation lead system including a percutaneous lead having three pairs of bipolar electrodes, with each pair at a different site;
    a health parameter detection system operative to detect parameters representative of at least one of heart failure, arrhythmia, hypertension, diabetes and cardiac ischemia of the patient; and
    a neurostimulation controller, operative in response to the detected parameter of the patient, to deliver neurostimulation to the one or more acupuncture sites using the neurostimulation lead system.

22. The implantable medical system of claim 21 wherein the implantable medical system includes a cardiac rhythm management device (CRMD) and wherein the health parameter detection system and the neurostimulation controller are components of the CRMD.

23. The system of claim 21 wherein the neurostimulation lead system includes two sternum (STN) leads with one implanted subcutaneously and the other implanted under the sternum.

24. The system of claim 21 wherein the neurostimulation lead system includes sternum (STN) leads implanted in pectoral regions of the patient.

25. The system of claim 21 wherein the neurostimulation lead system includes leads implanted in abdominal regions of the patient.

26. The system of claim 21 wherein the neurostimulation lead system includes surgical patches, the surgical patches being operable to generate paired current loops to induce magnetic field lines of force through selected stimulation sites for magnetic stimulation.

* * * * *